(12) United States Patent
Gulliver et al.

(10) Patent No.: US 11,690,995 B2
(45) Date of Patent: *Jul. 4, 2023

(54) CONDUIT CONNECTOR FOR A PATIENT BREATHING DEVICE

(71) Applicant: Fisher & Paykel Healthcare Limited, Auckland (NZ)

(72) Inventors: Laurence Gulliver, Auckland (NZ); Michael Paul Ronayne, Auckland (NZ); Charles William Douglas Irving, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 16 days.

This patent is subject to a terminal disclaimer.

(21) Appl. No.: 17/340,512

(22) Filed: Jun. 7, 2021

(65) Prior Publication Data

US 2021/0361924 A1 Nov. 25, 2021

Related U.S. Application Data

(63) Continuation of application No. 16/421,382, filed on May 23, 2019, now Pat. No. 11,052,236, which is a
(Continued)

(51) Int. Cl.
*A61M 39/10* (2006.01)
*A61M 16/08* (2006.01)
(Continued)

(52) U.S. Cl.
CPC ......... *A61M 39/1011* (2013.01); *A61B 5/082* (2013.01); *A61M 16/021* (2017.08);
(Continued)

(58) Field of Classification Search
CPC .......... A61M 39/1011; A61M 16/0833; A61M 16/0841; A61M 16/085;
(Continued)

(56) References Cited

U.S. PATENT DOCUMENTS 132,602 A 10/1872 Smith et al.
327,877 A 10/1885 Hodges
(Continued)

FOREIGN PATENT DOCUMENTS

CN 101365509 2/2009
CN 102019014 2/2009
(Continued)

OTHER PUBLICATIONS

PCT Application No. PCT/NZ2012/000142 International Search Report and Written Opinion dated Jan. 22, 2013, in 13 pages.
(Continued)

*Primary Examiner* — Beth A Stephan
(74) *Attorney, Agent, or Firm* — Knobbe, Martens, Olson & Bear, LLP

(57) ABSTRACT

In an embodiment, a connector or connector assembly for attaching a nasal cannula with a gas delivery hose includes a sensor port for a sensor probe positioned near an end of a nasal cannula, which can allow the sensor probe to be placed closer to the patient's nostrils than previous connector parts allowed. The connector can be configured to advantageously allow the nasal cannula to rotate relative to the gas delivery hose, thereby allowing a patient or healthcare provider to untangle or otherwise straighten the hose or the cannula. The connector assembly can be configured to automatically align locking protrusions on a first component with locking recesses on a second component, where insertion of the second component within the first component causes the second component to rotate relative to the first component, thereby aligning the locking protrusions with associated locking recesses.

20 Claims, 37 Drawing Sheets

Related U.S. Application Data continuation of application No. 15/730,553, filed on Oct. 11, 2017, now Pat. No. 10,335,583, which is a continuation of application No. 14/237,859, filed as application No. PCT/NZ2012/000142 on Aug. 10, 2012, now Pat. No. 9,808,612.

(60) Provisional application No. 61/521,972, filed on Aug. 10, 2011.

(51) Int. Cl.
  *A61M 16/16* (2006.01)
  *A61M 16/06* (2006.01)
  *A61M 16/00* (2006.01)
  *A61B 5/08* (2006.01)
  *A61M 16/10* (2006.01)

(52) U.S. Cl.
  CPC ...... *A61M 16/0666* (2013.01); *A61M 16/085* (2014.02); *A61M 16/0816* (2013.01); *A61M 16/0825* (2014.02); *A61M 16/0833* (2014.02); *A61M 16/0841* (2014.02); *A61M 16/161* (2014.02); *A61M 16/0051* (2013.01); *A61M 16/0875* (2013.01); *A61M 2016/0033* (2013.01); *A61M 2016/102* (2013.01); *A61M 2016/103* (2013.01); *A61M 2016/1025* (2013.01); *A61M 2039/1027* (2013.01); *A61M 2039/1044* (2013.01); *A61M 2205/3368* (2013.01); *A61M 2205/581* (2013.01); *A61M 2205/584* (2013.01); *A61M 2205/6045* (2013.01); *A61M 2209/088* (2013.01)

(58) Field of Classification Search
  CPC ...... A61M 2205/3368; A61M 16/0816; A61M 2205/581; A61M 2205/584; A61B 5/082
  See application file for complete search history.

(56) References Cited

U.S. PATENT DOCUMENTS

| | | |
|---|---|---|
| 1,880,098 A | 9/1932 | Mair |
| 2,124,474 A | 7/1938 | Scholtes |
| 2,479,580 A | 8/1949 | Marco |
| 2,727,759 A | 12/1955 | Elliott |
| 3,513,844 A | 5/1970 | Smith |
| 3,601,361 A | 8/1971 | Hundhausen et al. |
| 3,815,754 A | 6/1974 | Rosenberg |
| 4,036,616 A | 7/1977 | Byrns |
| 4,111,514 A | 9/1978 | Brishka et al. |
| 4,128,407 A | 12/1978 | Chapel |
| D267,199 S | 12/1982 | Koenig |
| 4,443,028 A | 4/1984 | Hayes |
| 4,446,869 A | 5/1984 | Knodle |
| 4,584,997 A | 4/1986 | Delong |
| 4,589,684 A | 5/1986 | Nowacki et al. |
| 4,601,495 A | 7/1986 | Webb |
| 4,661,110 A | 4/1987 | Fortier et al. |
| 4,773,448 A | 9/1988 | Francis |
| D300,271 S | 3/1989 | Rudolph et al. |
| D300,272 S | 3/1989 | Rudolph et al. |
| 5,040,527 A | 8/1991 | Larson et al. |
| 5,064,226 A | 11/1991 | Kias |
| D328,033 S | 7/1992 | DiGuiseppi |
| 5,158,569 A | 10/1992 | Strickland et al. |
| 5,281,206 A * | 1/1994 | Lopez .................. A61M 39/04 604/905 |
| 5,335,656 A | 8/1994 | Bowe et al. |
| D362,718 S | 9/1995 | Deily et al. |
| D363,541 S | 10/1995 | Cottone, Sr. et al. |
| 5,529,284 A | 6/1996 | Berger et al. |
| 5,584,997 A | 12/1996 | Yagihashi et al. |
| 5,725,258 A | 3/1998 | Kujawski |
| 5,735,271 A | 4/1998 | Lorenzen et al. |
| 5,901,705 A | 5/1999 | Leagre |
| D424,687 S | 5/2000 | Hoenig et al. |
| 6,099,519 A | 8/2000 | Olsen |
| D431,634 S | 10/2000 | Mantz |
| D449,107 S | 10/2001 | Madsen |
| 6,439,234 B1 | 8/2002 | Curt et al. |
| 6,484,724 B1 | 11/2002 | Sloan |
| D468,015 S | 12/2002 | Horppu |
| D472,316 S | 3/2003 | Douglas et al. |
| D472,630 S | 4/2003 | Douglas et al. |
| 6,561,549 B1 | 5/2003 | Moris et al. |
| 6,581,974 B1 | 6/2003 | Ragner |
| 6,893,055 B2 | 5/2005 | Thomas et al. |
| 6,915,705 B1 | 7/2005 | Truitt |
| 6,932,390 B1 | 8/2005 | Greiz |
| 6,953,354 B2 | 10/2005 | Edirisuriya |
| 7,007,694 B2 | 3/2006 | Aylsworth et al. |
| 7,201,167 B2 | 4/2007 | Fink et al. |
| D543,620 S | 5/2007 | Chu et al. |
| D547,657 S | 7/2007 | Tacchella |
| D551,340 S | 9/2007 | Wood et al. |
| 7,263,994 B2 | 9/2007 | Gradon et al. |
| 7,267,121 B2 | 9/2007 | Ivri |
| 7,290,541 B2 | 11/2007 | Ivri et al. |
| D556,899 S | 12/2007 | Veliss et al. |
| 7,306,121 B2 | 12/2007 | Ophardt |
| 7,311,752 B2 | 12/2007 | Tepper |
| D570,457 S | 6/2008 | Brown |
| 7,406,966 B2 | 8/2008 | Wondka |
| 7,458,615 B2 | 12/2008 | White et al. |
| D586,911 S | 2/2009 | McAuley et al. |
| D600,343 S | 9/2009 | Degabriele et al. |
| D612,481 S | 3/2010 | Reid et al. |
| 7,785,300 B2 | 8/2010 | Ishii et al. |
| D627,059 S | 11/2010 | Wood et al. |
| D631,452 S | 1/2011 | DeGross et al. |
| D631,542 S | 1/2011 | DeGross |
| D637,713 S | 5/2011 | Nord et al. |
| 7,946,291 B2 | 5/2011 | Fink et al. |
| D645,547 S | 9/2011 | Lombardi et al. |
| 8,020,551 B2 | 9/2011 | Virr et al. |
| D654,573 S | 2/2012 | Lombardi et al. |
| D661,785 S | 6/2012 | Johnson |
| 8,317,203 B2 | 11/2012 | Hermle et al. |
| D672,037 S | 12/2012 | Miller |
| 8,376,412 B2 | 2/2013 | Johnson |
| 8,397,727 B2 | 3/2013 | Ng et al. |
| D682,415 S | 5/2013 | Mogensen et al. |
| 8,439,039 B2 | 5/2013 | Gunaratnam et al. |
| D685,463 S | 7/2013 | Veliss et al. |
| 8,485,193 B2 | 7/2013 | Worley |
| 8,534,278 B2 | 9/2013 | Colman et al. |
| D691,717 S | 10/2013 | McLean et al. |
| D692,555 S | 10/2013 | Maksym |
| D695,890 S | 12/2013 | Bowden et al. |
| D697,200 S | 1/2014 | Mahaffy |
| D698,440 S | 1/2014 | Lombardi, III |
| 8,622,057 B2 | 1/2014 | Ujhazy et al. |
| D707,355 S | 6/2014 | Bow |
| 8,741,220 B2 | 6/2014 | O'Donnell et al. |
| D710,695 S | 8/2014 | Pritikin |
| D717,942 S | 11/2014 | Neff et al. |
| D724,720 S | 3/2015 | O'Connor et al. |
| 8,967,144 B2 | 3/2015 | Lurie |
| D726,287 S | 4/2015 | Steele |
| D727,492 S | 4/2015 | Scampoli |
| D735,038 S | 7/2015 | Tamarindo |
| D735,326 S | 7/2015 | Gulliver |
| D736,906 S | 8/2015 | Schultz |
| D736,914 S | 8/2015 | Schultz |
| D737,963 S | 9/2015 | Srinivasan et al. |
| 9,188,267 B2 | 11/2015 | Fansler et al. |
| D747,471 S | 1/2016 | Guiliver et al. |
| D747,794 S | 1/2016 | Greenberg |
| D750,239 S | 2/2016 | Pappalardo |
| D757,259 S | 5/2016 | Duck |
| D757,933 S | 5/2016 | Lev et al. |
| D759,486 S | 6/2016 | Ingram |

(56) References Cited

U.S. PATENT DOCUMENTS

| | | |
|---|---|---|
| D764,049 S | 8/2016 | Cullen et al. |
| D768,285 S | 10/2016 | Reed |
| D771,247 S | 11/2016 | Shinohara et al. |
| D777,317 S | 1/2017 | Soual et al. |
| D781,417 S | 3/2017 | Ingram |
| D785,161 S | 4/2017 | Dravitzki et al. |
| D785,789 S | 5/2017 | Turturro et al. |
| D787,053 S | 5/2017 | Huang et al. |
| D787,054 S | 5/2017 | Rini et al. |
| D790,054 S | 6/2017 | Prentice et al. |
| 9,669,181 B2 | 6/2017 | Miller et al. |
| 9,675,774 B2 | 6/2017 | Cipollone |
| D791,310 S | 7/2017 | Maurice |
| D791,938 S | 7/2017 | Becker |
| D791,939 S | 7/2017 | Turturro et al. |
| D794,184 S | 8/2017 | Smith et al. |
| D794,781 S | 8/2017 | Gilbert et al. |
| D800,895 S | 10/2017 | Prentice |
| D804,023 S | 11/2017 | Huang et al. |
| 9,808,612 B2 | 11/2017 | Gulliver et al. |
| D804,661 S | 12/2017 | Shoji et al. |
| D805,629 S | 12/2017 | Fiorenza |
| 9,879,807 B2 | 1/2018 | Brugger et al. |
| D809,656 S | 2/2018 | Lau et al. |
| 9,884,176 B2 | 2/2018 | Fangrow |
| D816,216 S | 4/2018 | Gulliver et al. |
| D825,749 S | 8/2018 | Huang et al. |
| D827,125 S | 8/2018 | Nilsson |
| D827,126 S | 8/2018 | Nilsson et al. |
| D832,431 S | 10/2018 | Turturro |
| D834,533 S | 11/2018 | Maroney |
| D834,712 S | 11/2018 | Gulliver et al. |
| D835,260 S | 12/2018 | Lisberg |
| D837,743 S | 1/2019 | Maroney |
| D841,148 S | 2/2019 | Stoks et al. |
| 10,245,407 B2 | 4/2019 | Osborne |
| 10,265,492 B2 | 4/2019 | Amarasinghe et al. |
| D849,242 S | 5/2019 | Wilson |
| D849,931 S | 5/2019 | Prentice |
| 10,322,254 B2 | 6/2019 | Fong et al. |
| D852,949 S | 7/2019 | Klenner et al. |
| 10,335,583 B2 | 7/2019 | Gulliver et al. |
| D855,794 S | 8/2019 | Gray |
| D856,510 S | 8/2019 | Scheirlinck |
| D857,880 S | 8/2019 | Lau et al. |
| D860,445 S | 9/2019 | Ho |
| D861,162 S | 9/2019 | Gulliver et al. |
| D863,545 S | 10/2019 | Dantanarayana |
| D867,583 S | 11/2019 | Yang et al. |
| D867,586 S | 11/2019 | Kemps et al. |
| D867,587 S | 11/2019 | Holtz et al. |
| D870,878 S | 12/2019 | Wilson |
| D878,549 S | 3/2020 | Wilson |
| D879,953 S | 3/2020 | Ljunglof et al. |
| D879,956 S | 3/2020 | Klenner et al. |
| D887,577 S | 6/2020 | Shor |
| D893,016 S | 8/2020 | Wilson |
| D896,758 S | 9/2020 | Watkins et al. |
| D896,929 S | 9/2020 | Vranish |
| 10,786,663 B2 | 9/2020 | Lauer |
| D899,590 S | 10/2020 | Gulliver et al. |
| 10,792,486 B2 | 10/2020 | Nelson |
| 10,835,733 B1 | 11/2020 | Gulliver et al. |
| D910,840 S | 2/2021 | Klenner et al. |
| D917,690 S | 4/2021 | Lau et al. |
| D925,734 S | 7/2021 | Park |
| 11,052,236 B2 | 7/2021 | Gulliver et al. |
| D928,948 S | 8/2021 | Guiliver et al. |
| D928,949 S | 8/2021 | Gulliver et al. |
| 2001/0004970 A1 | 6/2001 | Hollister |
| 2001/0029949 A1 | 10/2001 | Blackhurst et al. |
| 2002/0017302 A1 | 2/2002 | Fukunaga et al. |
| 2002/0112730 A1 | 8/2002 | Dutkiewicz |
| 2002/0173748 A1 | 11/2002 | McConnell |
| 2004/0090066 A1 | 5/2004 | Hoffmann |
| 2004/0103686 A1 | 6/2004 | Fehr et al. |
| 2004/0108218 A1 | 6/2004 | Stubergh |
| 2004/0261797 A1 | 12/2004 | White et al. |
| 2005/0011524 A1 | 1/2005 | Thomlinson et al. |
| 2005/0028822 A1 | 2/2005 | Sleeper et al. |
| 2005/0077726 A1 | 4/2005 | White et al. |
| 2005/0283114 A1 | 12/2005 | Bresina |
| 2006/0107958 A1 | 5/2006 | Sleeper |
| 2006/0107960 A1 | 5/2006 | Smart |
| 2006/0113690 A1 | 6/2006 | Huddart |
| 2007/0043334 A1 | 2/2007 | Guala |
| 2007/0088327 A1 | 4/2007 | Guala |
| 2007/0163588 A1 | 7/2007 | Hebrank et al. |
| 2007/0169825 A1 | 7/2007 | Packham et al. |
| 2007/0175473 A1 | 8/2007 | Lewis et al. |
| 2007/0276356 A1 | 11/2007 | Downing et al. |
| 2008/0041391 A1 | 2/2008 | Worley |
| 2008/0093846 A1 | 4/2008 | Sparks et al. |
| 2008/0142019 A1 | 6/2008 | Lewis et al. |
| 2008/0183153 A1 | 7/2008 | Enns |
| 2008/0190436 A1 | 8/2008 | Jaffe |
| 2008/0264413 A1 | 10/2008 | Doherty et al. |
| 2008/0287920 A1 | 11/2008 | Fangrow et al. |
| 2009/0101147 A1 | 4/2009 | Landis et al. |
| 2009/0120434 A1 | 5/2009 | Smith et al. |
| 2009/0223523 A1 | 9/2009 | Chang |
| 2009/0223963 A1 | 9/2009 | Bisio |
| 2009/0266357 A1 | 10/2009 | Varis et al. |
| 2009/0299158 A1 | 12/2009 | Boatner et al. |
| 2010/0043789 A1 | 2/2010 | Fine et al. |
| 2010/0116272 A1 | 5/2010 | Row et al. |
| 2010/0163051 A1 | 7/2010 | Brewer et al. |
| 2010/0168600 A1 | 7/2010 | Adriance et al. |
| 2010/0192957 A1 | 8/2010 | Hobson et al. |
| 2010/0206310 A1 | 8/2010 | Matsubara et al. |
| 2010/0242961 A1 | 9/2010 | Mougel et al. |
| 2011/0067704 A1 | 3/2011 | Kooij et al. |
| 2011/0139826 A1 | 6/2011 | Hair |
| 2011/0162644 A1 | 7/2011 | Ujhazy et al. |
| 2011/0253136 A1 | 10/2011 | Sweeney et al. |
| 2011/0265796 A1 | 11/2011 | Amarasinghe et al. |
| 2012/0247477 A1 | 10/2012 | Stephenson et al. |
| 2012/0305001 A1 | 12/2012 | Tatkov |
| 2012/0326438 A1 | 12/2012 | Robert et al. |
| 2013/0037030 A1 | 2/2013 | Matula |
| 2013/0104888 A1 | 5/2013 | Landis et al. |
| 2013/0133651 A1 | 5/2013 | Barker et al. |
| 2013/0167841 A1 | 7/2013 | Sheffer et al. |
| 2013/0255670 A1 | 10/2013 | Ott et al. |
| 2013/0264821 A1 | 10/2013 | Duck |
| 2013/0284167 A1 | 10/2013 | Porteous et al. |
| 2014/0000626 A1 | 1/2014 | O'Connor et al. |
| 2014/0014108 A1 | 1/2014 | Dillard |
| 2014/0053846 A1 | 2/2014 | Wood |
| 2014/0144438 A1 | 5/2014 | Klasek |
| 2014/0191501 A1 | 7/2014 | Brugger et al. |
| 2014/0200475 A1 | 7/2014 | Rubin |
| 2014/0238401 A1 | 8/2014 | Paschall |
| 2014/0261416 A1 | 9/2014 | Arcilla et al. |
| 2014/0338669 A1 | 11/2014 | Zhao et al. |
| 2014/0373841 A1 | 12/2014 | Nashed |
| 2015/0021909 A1 | 1/2015 | Gulliver et al. |
| 2015/0059745 A1 | 3/2015 | Barker et al. |
| 2015/0083121 A1 | 3/2015 | Fisher |
| 2015/0128944 A1 | 5/2015 | Buechi |
| 2015/0167877 A1 | 6/2015 | Kendrick |
| 2015/0290416 A1 | 10/2015 | Klasek |
| 2015/0306332 A1 | 10/2015 | Bafile et al. |
| 2015/0320949 A1 | 11/2015 | Jaffe |
| 2015/0320962 A1 | 11/2015 | Bafile et al. |
| 2016/0082218 A1 | 3/2016 | Lau |
| 2016/0106913 A1 | 4/2016 | Ng et al. |
| 2016/0131292 A1 | 5/2016 | Decker |
| 2016/0228668 A1 | 8/2016 | Martin |
| 2016/0287824 A1 | 10/2016 | Chang |
| 2016/0305574 A1 | 10/2016 | Burdge |
| 2017/0036007 A1 | 2/2017 | Hallisey et al. |
| 2017/0065788 A1 | 3/2017 | Chou |
| 2017/0065789 A1 | 3/2017 | Reed |

(56) References Cited

U.S. PATENT DOCUMENTS

| | | |
|---|---|---|
| 2017/0197055 A1 | 7/2017 | Moody |
| 2017/0361051 A1 | 12/2017 | Eifler |
| 2018/0078728 A1 | 3/2018 | Holyoake et al. |
| 2018/0085544 A1 | 3/2018 | Holyoake |
| 2018/0117270 A1 | 5/2018 | Bassin |
| 2018/0140819 A1 | 5/2018 | Yang |
| 2018/0200148 A1 | 7/2018 | Sanders |
| 2019/0022344 A1 | 1/2019 | Lau et al. |
| 2019/0167935 A1 | 6/2019 | Siew et al. |
| 2019/0381268 A1 | 12/2019 | Colman |
| 2020/0129724 A1 | 4/2020 | Nelson |

FOREIGN PATENT DOCUMENTS

| | | |
|---|---|---|
| CN | 101380497 A | 3/2009 |
| CN | 102019014 | 4/2011 |
| CN | 201775849 | 4/2011 |
| CN | 103180650 A | 6/2013 |
| CN | 103764213 A | 4/2014 |
| CN | 103857432 A | 6/2014 |
| CN | 104853796 A | 8/2015 |
| CN | 104870042 A | 8/2015 |
| DE | 37 09 122 A1 | 9/1988 |
| DE | 10 2007 063 556 A1 | 7/2009 |
| EM | 008110019-0001 | 9/2020 |
| EP | 1 068 889 | 1/2001 |
| EP | 1 181 945 A1 | 2/2002 |
| EP | 0 809 768 B1 | 7/2002 |
| EP | 1 314 446 | 8/2002 |
| EP | 1 277 488 | 1/2003 |
| EP | 1 403 838 | 3/2004 |
| EP | 1 408 313 | 4/2004 |
| EP | 1 408 313 A2 | 4/2004 |
| EP | 1 520 599 A1 | 10/2004 |
| EP | 1 479 405 A1 | 11/2004 |
| EP | 1 481 702 | 12/2004 |
| EP | 1 023 912 B1 | 11/2005 |
| EP | 1 449 502 | 12/2007 |
| EP | 2 741 802 B1 | 10/2017 |
| EP | 1 933 074 | 6/2018 |
| EP | 2 925 396 | 9/2020 |
| GB | 2328260 | 2/1999 |
| JP | 09-028806 | 2/1997 |
| JP | 2007-236567 A | 9/2007 |
| JP | 2010-527276 A | 8/2010 |
| JP | 2014-516601 A | 7/2014 |
| JP | 2014-521471 A | 8/2014 |
| JP | D1639030 | 8/2019 |
| KR | 1020040103139 | 12/2004 |
| WO | WO 94/004211 | 3/1994 |
| WO | WO 97/015376 | 5/1997 |
| WO | WO 99/012598 | 3/1999 |
| WO | WO 90/014122 | 11/1999 |
| WO | WO 2003/082406 | 10/2003 |
| WO | WO 2004/108218 | 12/2004 |
| WO | WO 05/018524 | 3/2005 |
| WO | WO 2005/079670 | 9/2005 |
| WO | WO 05/102431 | 11/2005 |
| WO | WO 07/019625 | 2/2007 |
| WO | WO 07/024812 | 3/2007 |
| WO | WO 2008/144447 A2 | 11/2008 |
| WO | WO 09/094532 | 7/2009 |
| WO | WO 09/146484 | 12/2009 |
| WO | WO 11/062510 | 5/2011 |
| WO | WO 2011/079226 | 6/2011 |
| WO | WO 12/052903 | 4/2012 |
| WO | WO 2013/022356 | 2/2013 |
| WO | WO 13/088439 | 6/2013 |
| WO | WO 13/127474 | 9/2013 |
| WO | WO 14/015382 | 1/2014 |
| WO | WO 14/077706 | 5/2014 |
| WO | WO 2014/097145 | 6/2014 |
| WO | WO 2014/129912 | 8/2014 |
| WO | WO 15/038014 | 3/2015 |
| WO | WO 16/157101 | 10/2016 |
| WO | WO 2017/037660 A1 | 3/2017 |

OTHER PUBLICATIONS

Fisher & Paykel Healthcare Limited, Junior Tube and Chamber Kit brochure, 900PT531, 2012.
PCT Application No. PCT/NZ2012/000142 International Preliminary Report on Patentability dated Feb. 14, 2014 in 6 pages.
Examination Report in corresponding Australian Patent Application No. 2017202180, dated Aug. 31, 2018, in 3 pages.
Office Action in corresponding Australian Patent Application No. 2017202180, dated Jul. 19, 2019, in 3 pages.
Office Action in corresponding Canadian Patent Application No. 2844802, dated Jun. 6, 2018, in 4 pages.
Office Action in corresponding Canadian Patent Application No. 2,844,802, dated Jun. 12, 2019, in 4 pages.
Examination Report in corresponding Canadian Patent Application No. 2844802, dated Jul. 27, 2020, in 6 pages.
Examination Report in corresponding Chinese Patent Application No. 201710181760.0, dated May 29, 2019, in 5 pages.
Office Action in corresponding Chinese Patent Application No. 201710181760.0, dated Dec. 19, 2019, in 18 pages.
Examination Report in corresponding Chinese Patent Application No. 201710181760.0, dated Aug. 24, 2020, in 7 pages.
Examination Report in corresponding Chinese Patent Application No. 201680060677.1, dated Nov. 16, 2020, in 8 pages.
Examination Report in corresponding Chinese Patent Application No. 201710181804.X, dated May 29, 2019, in 8 pages.
Examination Report in corresponding Chinese Patent Application No. 201710181804.X, dated Jan. 10, 2020, in 8 pages.
Examination Report in corresponding Chinese Patent Application No. 201710181804.X, dated Sep. 1, 2020, in 3 pages.
Extended Search Report in corresponding European Patent Application No. 17195173.4, dated May 22, 2018, in 13 pages.
Combined Search and Examination Report in corresponding United Kingdom Patent Application No. GB 10800268.3, dated Jan. 25, 2018, in 6 pages.
Examination Report in corresponding United Kingdom Patent Application No. GB 10800268.3, dated Jun. 8, 2018, in 3 pages.
Examination Report in corresponding United Kingdom Patent Application No. 1800268.3, dated Jul. 3, 2018, in 2 pages.
Office Action in corresponding United Kingdom Patent Application No. 1807231.4, dated Jun. 19, 2018, in 9 pages.
Examination Report in corresponding United Kingdom Patent Application No. 1807231.4, dated Aug. 31, 2018, in 2 pages.
Examination Report in corresponding United Kingdom Patent Application No. 1810896.9, dated Nov. 20, 2018, in 5 pages.
Examination Report in United Kingdom Patent Application No. 1803152.6, dated Oct. 26, 2020, in 2 pages.
Office Action in corresponding Japanese Patent Application No. 2014-524961, dated Nov. 8, 2017, in 2 pages.
Office Action in corresponding Japanese Patent Application No. 2018-041463, dated Jan. 31, 2019, in 2 pages.
Decision for Final Rejection in corresponding Japanese Patent Application No. 2018-041463, dated Aug. 1, 2019, in 2 pages.
Office Action in corresponding Taiwanese Patent Application No. 1061015308, dated Apr. 12, 2007, in 4 pages.
Search Report in corresponding Taiwanese Patent Application No. 1061015308, dated Apr. 12, 2007, in 1 page.
Examination Report in corresponding Taiwanese Patent Application No. 106105308, dated Aug. 10, 2018, in 6 pages.
Examination Report in corresponding Taiwanese Patent Application No. 106105308, dated Feb. 11, 2020, in 7 pages.
Pall Corporation, Jun. 10, 2019, Multiple-Patient-Use Anesthesia Circuits, product description, 5 pp.
Salter Labs, "Air-Q Intubating Laryngeal Airways (ILA) The everyday airway that's ready for the unexpected."; Dec. 2018; 8 pages.

* cited by examiner

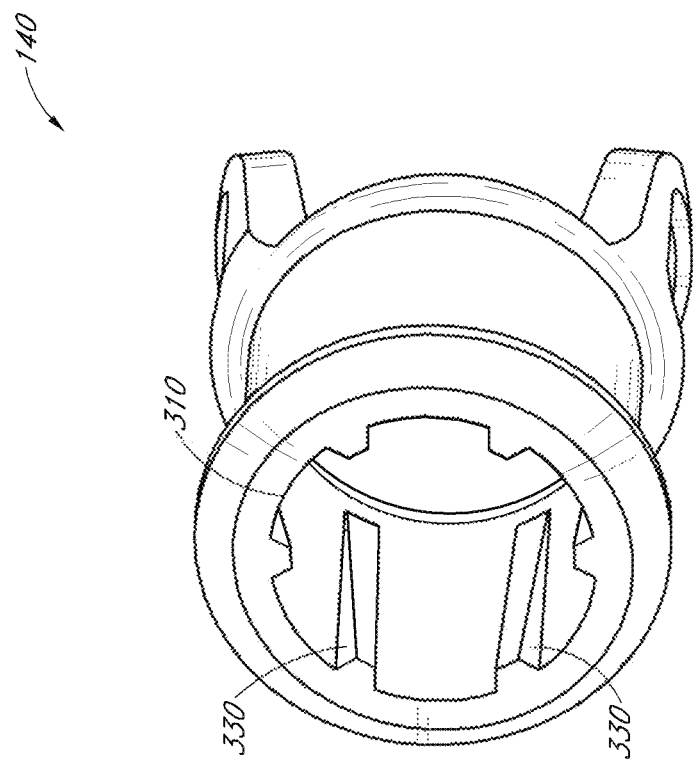
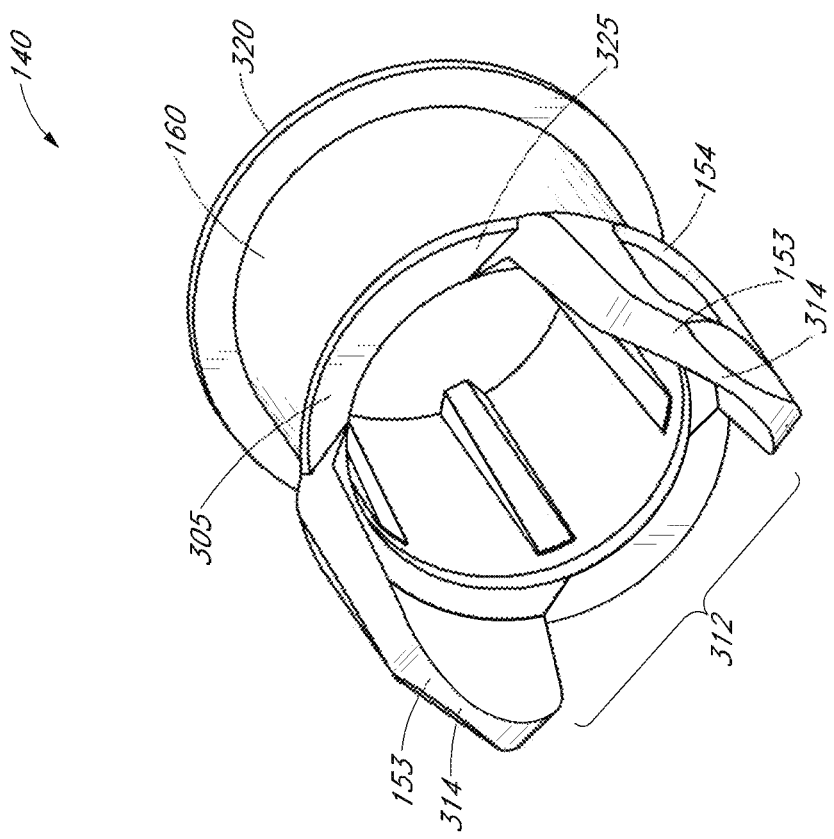
FIG. 3B
FIG. 3A

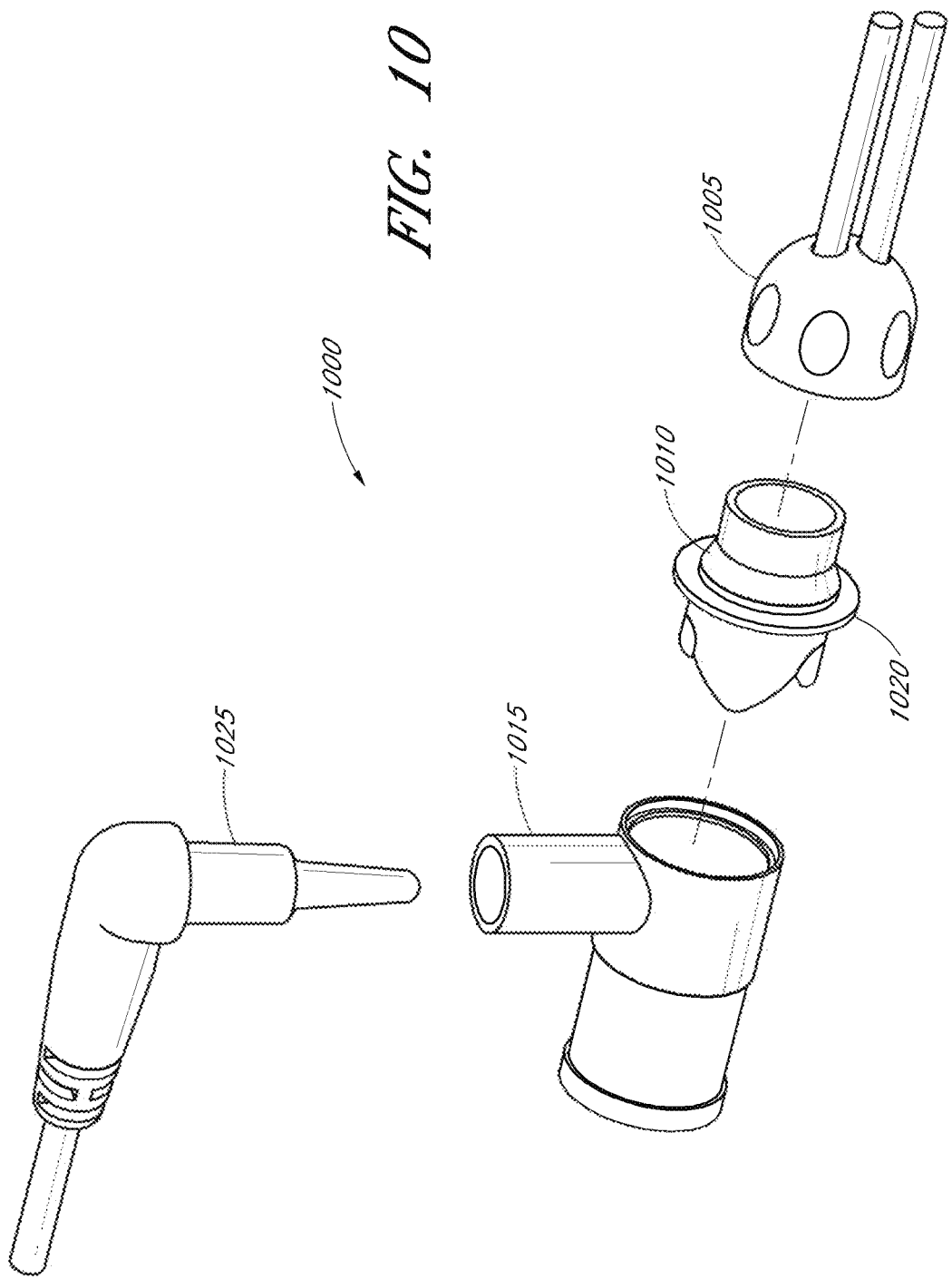

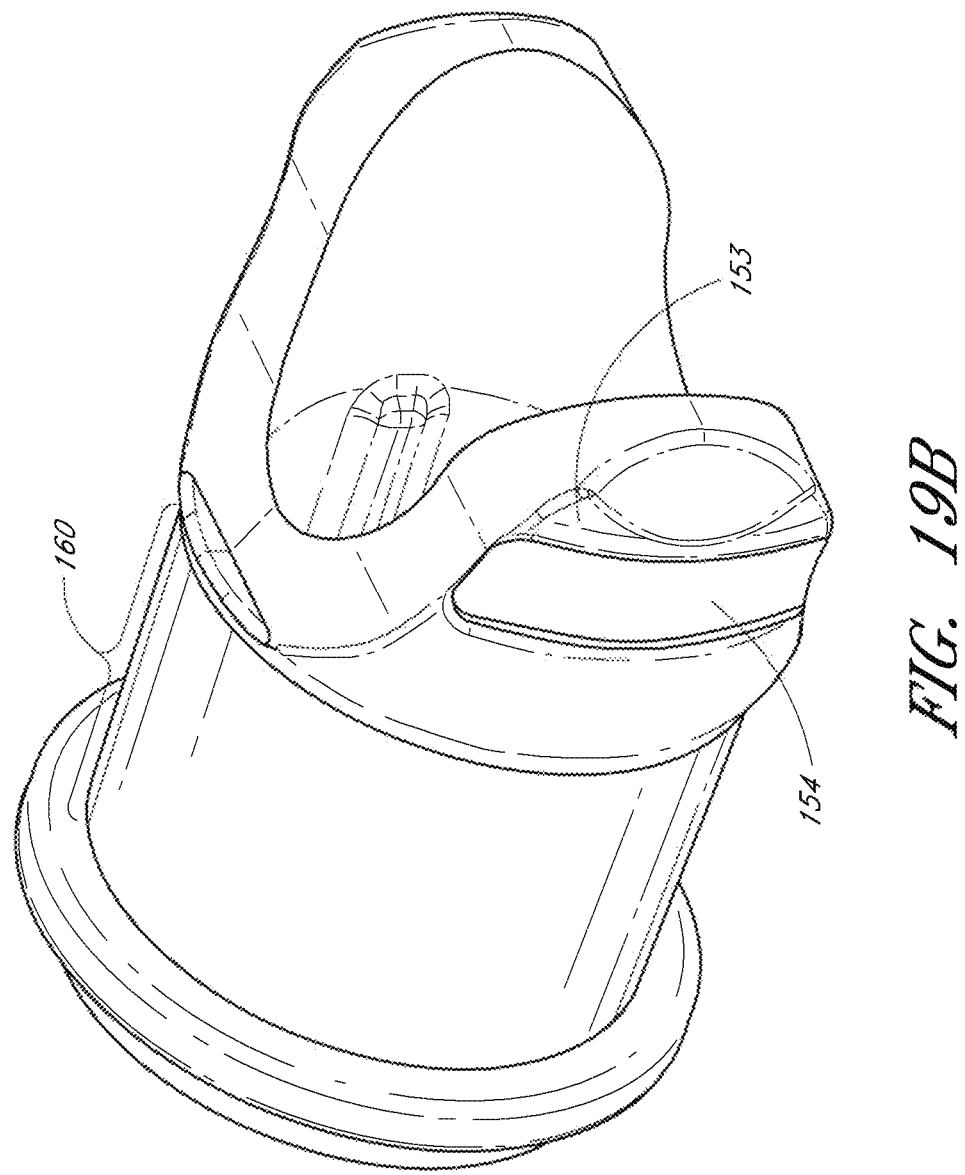

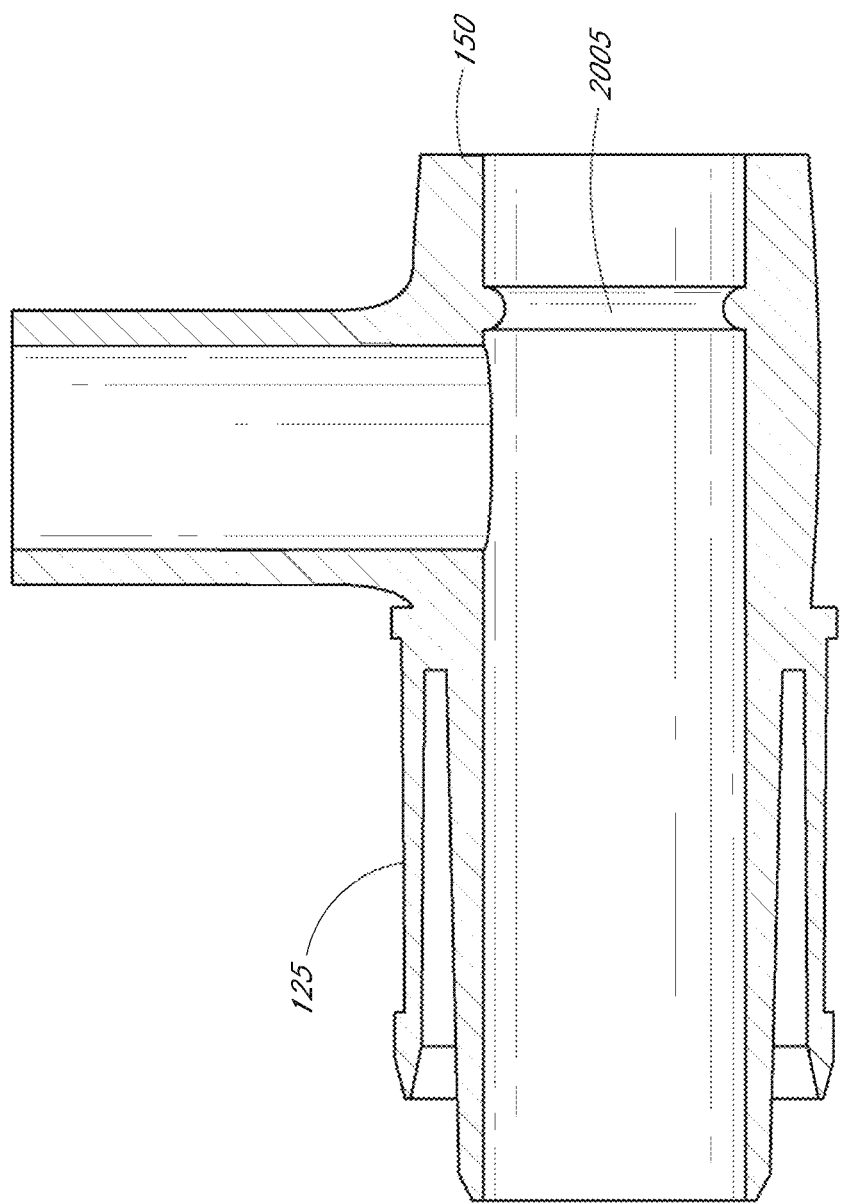

CONDUIT CONNECTOR FOR A PATIENT BREATHING DEVICE

CROSS-REFERENCE TO RELATED APPLICATIONS

This application is a continuation of U.S. application Ser. No. 16/421,382, filed May 23, 2019, now U.S. Pat. No. 11,052,236, which is a continuation of U.S. application Ser. No. 15/730,553, filed Oct. 11, 2017, now U.S. Pat. No. 10,335,583, which is a continuation of U.S. application Ser. No. 14/237,859, filed Aug. 20, 2014, now U.S. Pat. No. 9,808,612, which is a national phase of International Application No. PCT/NZ2012/000142, filed Aug. 10, 2012, which claims priority from U.S. Provisional App. No. 61/521,972, filed Aug. 10, 2011. Each of the applications referenced in this paragraph is incorporated by reference herein in its entirety.

FIELD OF THE DISCLOSURE

This disclosure relates to the field of connectors for gas delivery hoses.

BACKGROUND OF THE DISCLOSURE

A nasal cannula is a device used to deliver supplemental oxygen, other gases, or airflow to a patient or person for treatment or for aiding respiration. Typically, the cannula includes a plastic tube and a set of two prongs which are placed in the nostrils. Oxygen or other gases can flow from these prongs.

The nasal cannula can be connected to an oxygen tank, a portable oxygen generator, a wall connection in a hospital via a flowmeter, or other gas source. Nasal cannulas can supply oxygen to a patient at rates that depend partly on size. For example, infant or neonatal nasal versions can carry less oxygen and can have smaller prongs than adult versions. The cannula can be used to supply oxygenated air, humidified air or other gas mixtures.

SUMMARY OF THE DISCLOSURE

In some situations, a nasal cannula is used to provide humidified airflow or oxygen therapy. In order to monitor the airflow being received by the patient, a sensor probe can be used. However, the further the distance of the probe from the prongs that provide air to the nostrils, the greater the potential variance between the sampled air and the air inhaled by the patient. Thus, a conduit connector that places the sensor probe in the airflow closer to the patient can enhance the accuracy of the measurements taken.

As a nasal cannula or other breathing device can be connected to a patient for extended periods of time, the nasal cannula can generate discomfort for the patient or otherwise begin to perform sub-optimally. For example, as the patient moves around in a hospital bed, the nasal cannula tubing can become tangled or twisted, thereby causing the patient discomfort or limiting the airflow within the cannula. Thus, a design that facilitates adjustments of the nasal cannula can provide greater comfort to the patient or improve performance.

At times, the nasal cannula or an airflow source may need to be removed or replaced. If detaching the nasal cannula from the airflow source is difficult or time consuming, detaching the nasal cannula may cause significant discomfort for the patient. Further, in emergencies, a slow or difficult connection mechanism can potentially place the patient's health in danger. Thus, a conduit connector that provides a "quick-connect" or "quick-release" feature that facilitates attachment and detachment of the nasal cannula from an airflow source, as well as facilitating interchangeability of components, can provide greater comfort and/or safety.

In order to address the issues discussed above, aspects of the present disclosure include a connector or connector assembly for attaching a nasal cannula with a gas delivery hose. In an embodiment, the connector assembly includes a sensor port for a sensor probe. The sensor port is positioned near an end of a nasal cannula, towards the patient. In an embodiment, the connector is configured to allow the sensor to be placed closer to the patient's nostrils than previous connector parts allowed.

Aspects of the present disclosure also include a self-aligning connector assembly configured to automatically align locking protrusions on a first component with locking recesses on a second component, wherein insertion of the second component within the first component causes the second component to rotate relative to the first component, thereby aligning the locking protrusions with associated locking recesses. In an embodiment, the connector is configured to advantageously allow the nasal cannula to rotate relative to the gas delivery hose. By allowing rotation, the connector enables a patient or healthcare provider to untangle or otherwise straighten the hose or the cannula, thereby increasing patient comfort.

BRIEF DESCRIPTION OF THE DRAWINGS

Throughout the drawings, reference numbers may be re-used to indicate correspondence between referenced elements. The drawings are provided to illustrate embodiments of the disclosure described herein and not to limit the scope thereof.

FIGS. 3A and 3B illustrate perspective views of the connecting adapter of FIG. 1A from a source aperture side and a terminal aperture side, respectively;

FIGS. 7-16 illustrate alternate connector embodiments;

FIGS. 19A-19B illustrate an alternate connector adapter embodiment configured to connect with the source conduit connector embodiment of FIGS. 20A-20B;

FIGS. 20A-20B illustrate an alternate source conduit connector embodiment having an annular ring for attaching to the alternate connector adapter embodiment of FIGS. 19A-19B;

DETAILED DESCRIPTION

Figure 1A:
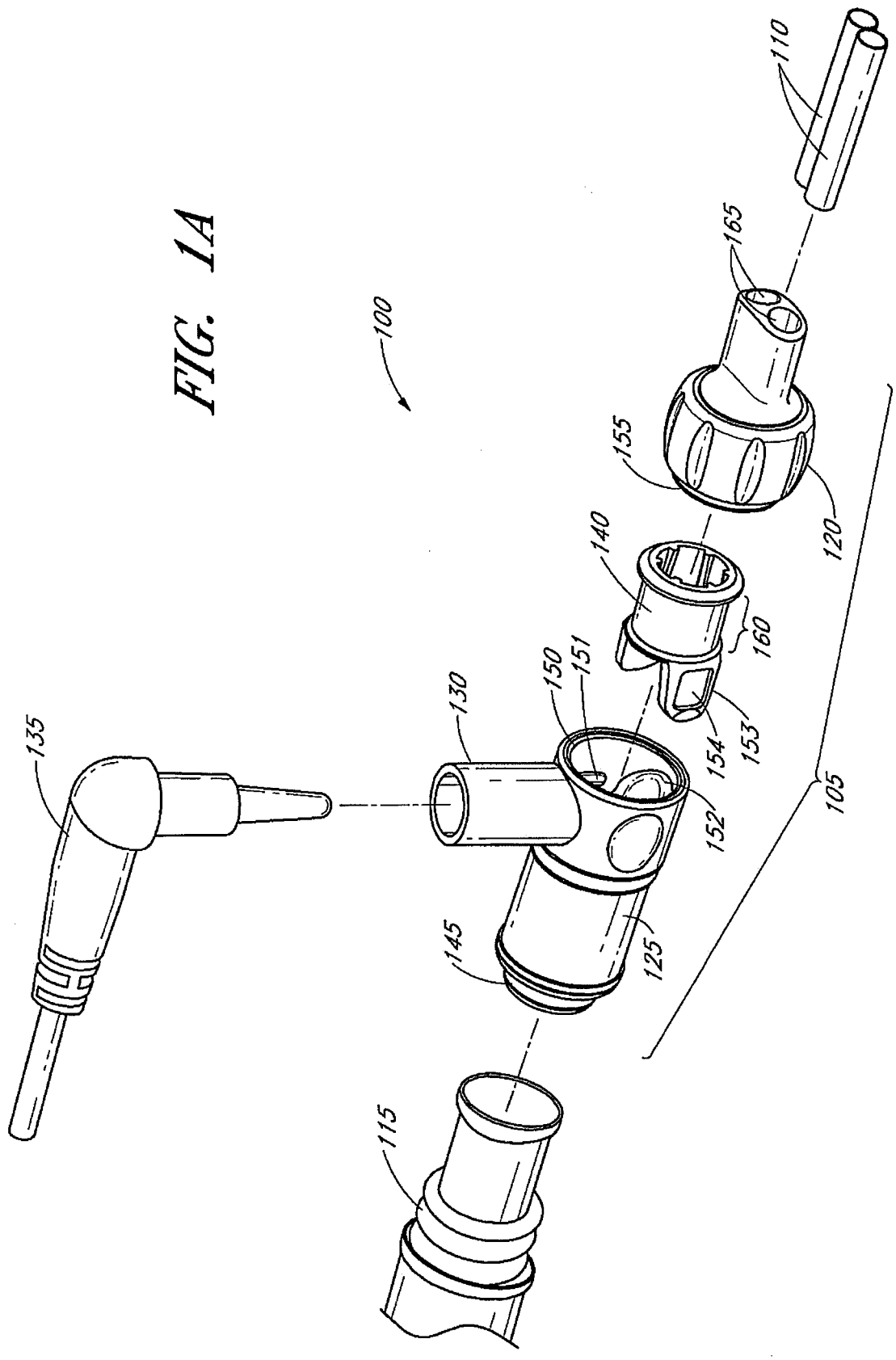
FIG. 1A illustrates an exploded perspective view of a gas delivery conduit having a connector embodiment for attaching a first tube with a second tube, the connector having a source conduit connector, a terminal conduit connector and a connecting adapter.
Figure 1B:
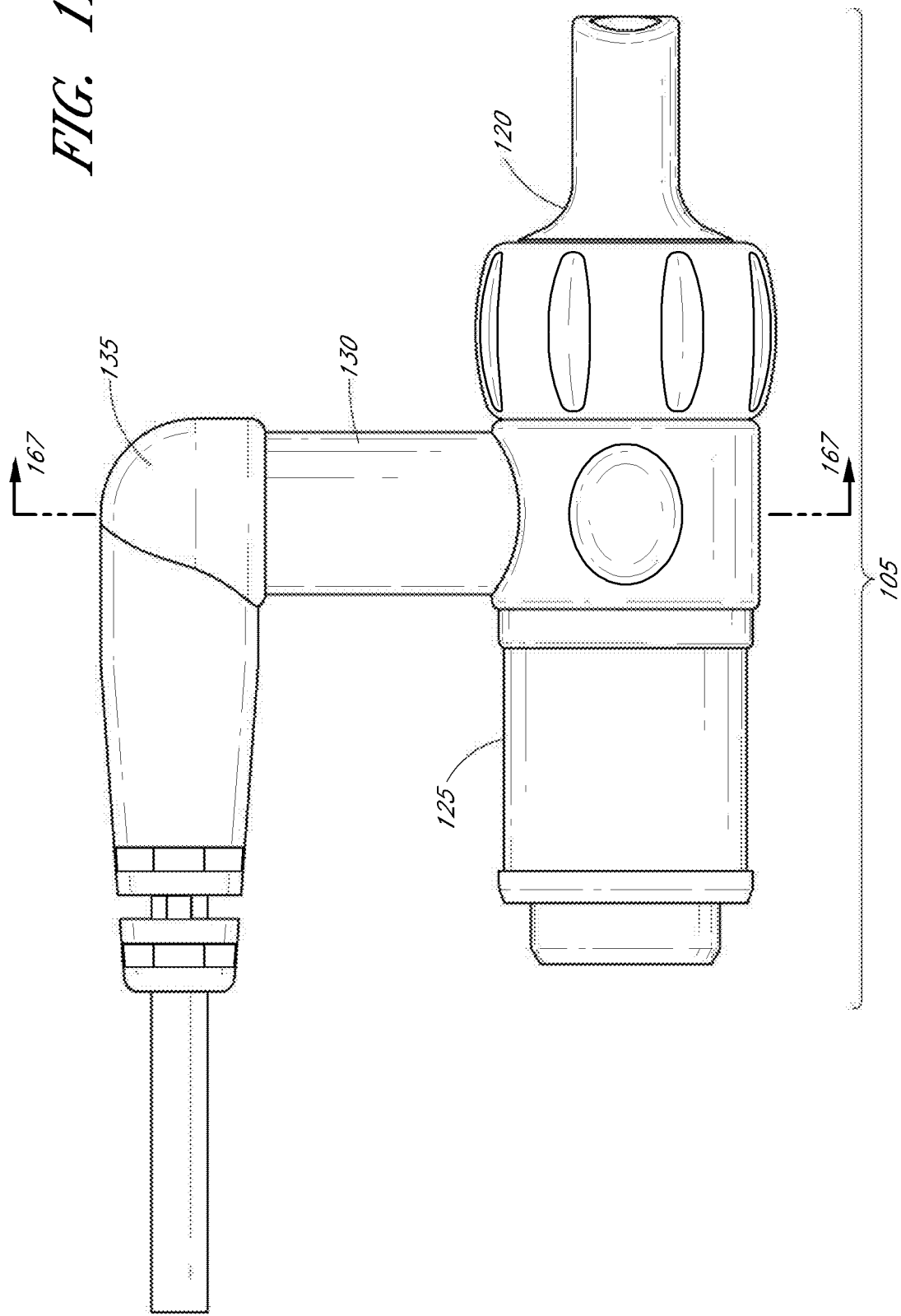
FIG. 1B illustrates a side view of the connector embodiment of FIG. 1A.

FIGS. 1A and 1B illustrate a perspective view and side view, respectively, of a gas delivery conduit 100 comprising an embodiment of a connector 105 for attaching a first tube 110 from a nasal cannula, face mask, intubation tube or other breathing device for a patient with a second tube 115 from a respirator, humidifier, breathing circuit, or other airflow device for providing gas to the patient. The connector can allow components of the gas delivery conduit 100 to be connected or disconnected from each other, thus facilitating disconnection and reconnection of the breathing device and airflow device with potentially minimal disturbance to the patient or gas delivery system.

For example, a patient can receive humidified, oxygenated and/or pressurized gases through a nasal cannula 110 connected to the gas delivery tube 115 that in turn is connected to a humidifier or respirator. For ease of explanation, the following disclosure refers to embodiments of the connector for connecting a nasal cannula with a gas delivery tube (e.g., for providing oxygen), but references to such embodiments are not intended to limit the disclosure and other embodiments are possible. For example, in other embodiments, gases are supplied to the patient by alternative patient interfaces, such as a nasal or full-face mask, or provided using alternative airflow sources.

In the illustrated embodiment, the connector 105 includes a terminal conduit connector 120 for receiving a nasal cannula 110, a source conduit connector 125 for receiving a gas delivery tube 115 and a connecting adapter 140 for connecting the conduit connectors. The source conduit connector 125 includes an optional sensor port 130 for receiving a sensor probe 135. In the illustrated embodiment, the terminal conduit connector 120 and source conduit connector 125 are releasably connected by the connecting adapter 140. The gas delivery tube 115 is configured to connect with the source conduit connector 125 and the nasal cannula 110 is configured to connect with the terminal conduit connector 120, forming a gas conduit 100 for providing oxygen or other gases to a patient. Generally, the oxygen flows from the gas delivery tube 115 to the nasal cannula 110. For ease of explanation, apertures of components of the gas conduit proximal to the gas delivery tube 115 are referred to as source apertures while apertures proximal to the nasal cannula 110 are referred to as terminal apertures.

In the illustrated embodiment, a source aperture 145 of the source conduit connector 125 connects with the gas delivery tube 115, for example, by fitting over and/or around the gas delivery tube 115 to form a seal. The source conduit connector 125 may be releasably attached to the gas delivery tube 115 or permanently attached. In one embodiment, the terminal aperture 150 of the source conduit connector 125 includes locking tabs 151 and/or alignment tabs 152 for receiving the connecting adapter 140. In one embodiment, the locking tabs are configured to lock with locking recesses 154 formed on fingers 153 of the connecting adapter 140, thereby forming a releasable seal. In one embodiment, the alignment tabs 152 are configured to cause the connecting adapter 140 to rotate within the terminal aperture 150 if the locking tabs are misaligned with the locking recesses when inserted into the terminal aperture 150. The alignment tabs cause the connecting adapter 140 to rotate until the locking tabs and locking recess are aligned. In an embodiment, the recesses 154 are holes extending through the fingers 153 and configured to perform the same function as the recesses 154.

In one embodiment, the locking tabs are configured to engage with the locking recesses 154 with an audible click in order to provide positive feedback that a connection has been fully made. Such a click can be generated, in one embodiment, when the fingers 153 are biased as they pass over the locking tabs and then generate a click when the locking recesses 154 snap-fit over the locking tabs. Audible clicks can also be generated in other ways, such as when other components engage with each other.

In the illustrated embodiment, a source aperture 155 of the terminal conduit connector is configured to receive the connecting adapter 140 to form a rotatable connection. In one embodiment, ridges formed within the terminal conduit connector are adapted to lock with a channel 160 formed on the circumference of the connecting adapter 140. The terminal conduit connector 120 and connecting adapter 140 are able to rotate relative to each other by allowing the ridges to rotate along the channel 160. In one embodiment, raised edges or collars along a terminal and source apertures of connecting adapter 140 prevent or inhibit disconnection of the terminal conduit connector 120 from the connecting adapter 140.

The terminal conduit connector 120 can include a terminal aperture configured to receive a cannula tube of a nasal cannula 110. The terminal aperture 165 can include two openings for receiving a double conduit cannula tube. Each conduit can connect to a prong for insertion into a patient's nostril. The nasal cannula 110 can be releasably attached to the terminal conduit connector 120 or permanently attached.

Figure 6:
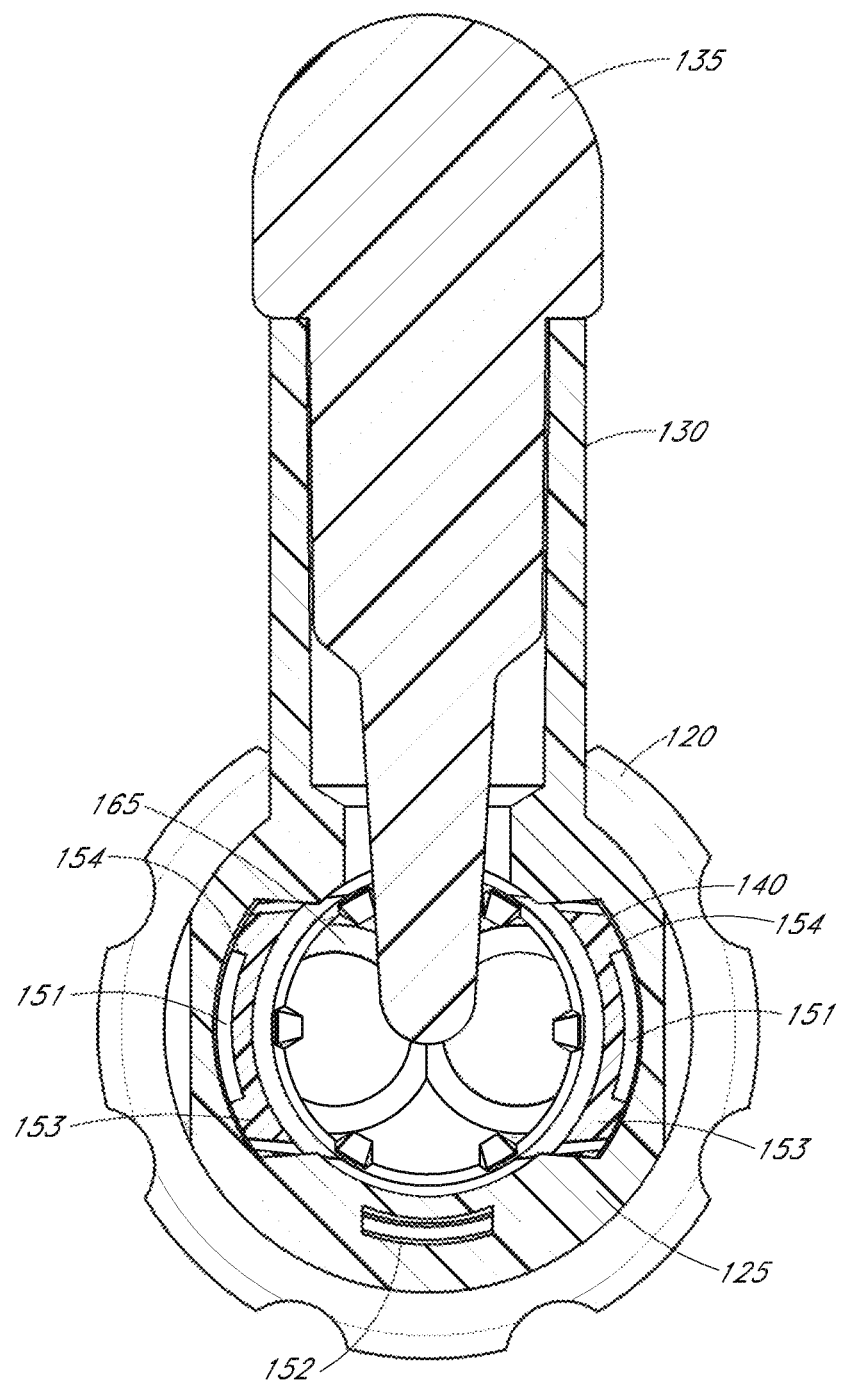
FIG. 6 illustrates a cross-section taken along across an axis of FIG. 1B and illustrates the engagement of the connecting adapter with the source conduit connector.

FIG. 1B illustrates a side view of the connector 105. The source conduit connector 125 is connected to the terminal conduit connector 120. The sensor probe 135 is connected to the connector 105 via the sensor port 130. Axis 167 illustrates the cross-section along which FIG. 6 is taken.

Figure 1C:
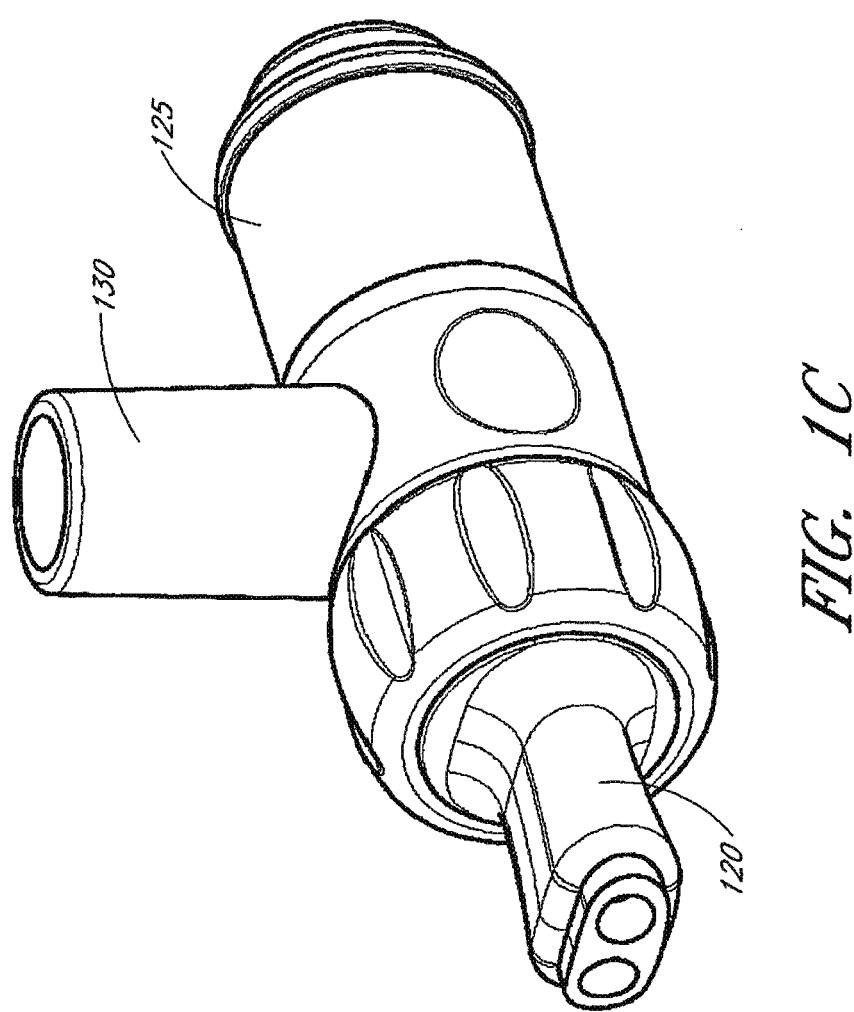
FIG. 1C illustrates a perspective view of another connector embodiment having other embodiments of the source conduit connector, the terminal conduit connector and the connecting adapter.

FIG. 1C illustrates a perspective view of another connector embodiment having other embodiments of the source conduit connector 125, the terminal conduit connector 120 and the connecting adapter 140 (hidden in this view). This embodiment shares many of the structures and features discussed above with respect to FIG. 1A, such as the sensor port 130.

Figure 2A:
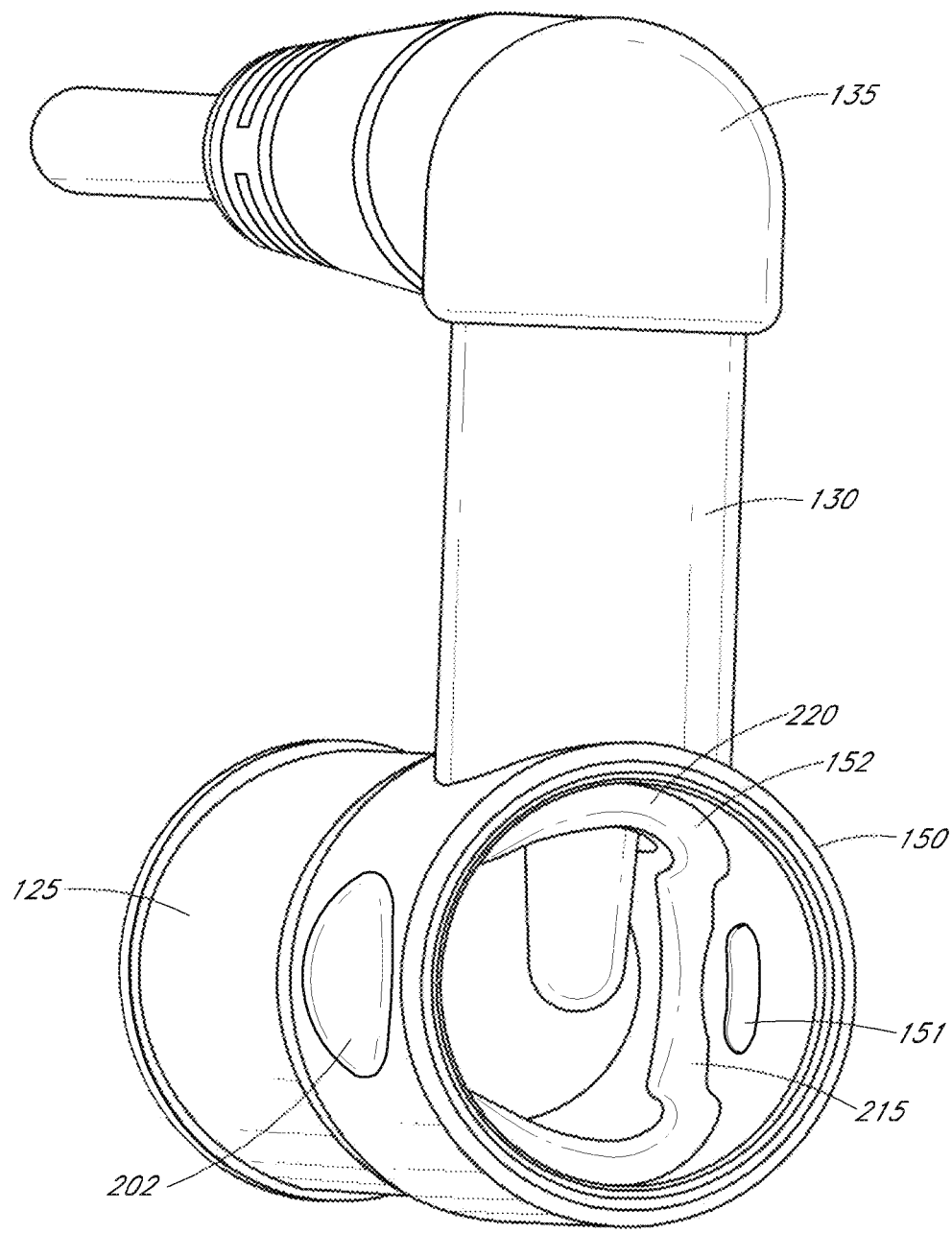
FIG. 2A illustrates a perspective view of the terminal aperture side of the source conduit connector of FIG. 1A.

FIG. 2A illustrates a perspective view of the terminal aperture 150 side of the source conduit connector 125 of FIG. 1A. In the illustrated embodiment, the source conduit connector 125 includes a substantially cylindrical tube having a terminal aperture 150 and a source aperture 145 (FIG. 1A). The source conduit connector 125 can also include an optional sensor port 130 for receiving a sensor probe 135. In FIG. 2A, the sensor port 130 includes a substantially cylindrical tube extending perpendicularly from the source conduit connector 125. In some embodiments, the tube is perpendicular to the body of the conduit connector 125. In some embodiments, the tube is substantially perpendicular but may be angled by a few degrees (e.g., less than 5, 10, or 15 degrees) from perpendicular. In some embodiments, the tube is angled by more than 15 degrees. One or more finger grooves 202 can be formed on the outside surface of the source conduit connector 125 in order to provide additional purchase or friction to a user, for example, for connecting or disconnecting the connector 105 (FIG. 1A) components. For example, two finger grooves 202 can be placed on opposite sides of the source conduit connector 125.

In the illustrated embodiment, the source conduit connector 125 includes locking tabs 151 and alignment tabs 152 for receiving the connecting adapter 140 (FIG. 1A). In FIG. 2A, two locking tabs 151 are formed on the interior surface of the source conduit connector 125 and configured to lock with locking recesses formed on the connecting adapter 140. The locking tabs 151 can be formed opposite each other.

In FIG. 2A, the alignment tab 152 is formed by a single, continuous protrusion or ridge formed on the interior surface of the source conduit connector 125. In one embodiment, the single continuous protrusion or ridge alternates from a first distance toward the terminal aperture 150 of the source conduit connector 125 to a second distance away from the terminal aperture 150. The continuous protrusion or ridge can form a bowl or saddleback shape, with alternating valleys 215 and apexes 220. The apexes 220 are configured to direct fingers of the connecting adapter 140 into the valleys 215, wherein the locking tabs 151 can lock with locking recesses on the fingers. For example, the apexes 220 can be sloped towards the valleys 215, such that the fingers, when inserted into the source conduit connector 125, are directed by the slope of the apexes 220 towards the valleys 215.

In FIG. 2A, the source conduit connector 125 includes an optional sensor port 130 for receiving a sensor probe 135. In the illustrated embodiment of FIG. 2A, the sensor port 130 is positioned near the terminal aperture 150 or substantially adjacent to the aperture 150. By placing the sensor port 130 close to the aperture 150, the sensor probe 135 is able to sample gas flow closer to the patient. Such sampling can provide more accurate measurement of the condition of the gas flow that the patient receives. For example, if the sensor probe 135 is positioned further away from the patient, there may be a greater difference between the sampled gas flow and the gas flow inhaled by the patient. Thus, gas flow that appears to be within the patient's comfort zone (e.g., based on temperature or humidity) may cause discomfort to the patient as the condition of the measured gas flow is different from the condition of the inhaled gas flow. In one example, the airflow source 115 can include a heating element that warms the air, but as the airflow leaves the source 115, the temperature of the airflow can cool rapidly. As a result, in one embodiment, the sensor should be placed as close to the patient as possible to obtain more accurate results. Similarly, due to condensation, humidity changes occur very rapidly. Again, the closer the sensor can be placed to the patient, the more accurate the sensor measurements will be. As will be apparent, similar benefits can be obtained without the optional sensor port 130 by positioning the sensor probe 135 close to the aperture 150 or towards the patient or nasal cannula 110. For example, this can be done by replacing the sensor port with an integrated sensor as described below.

As illustrated in FIG. 2A, the sensor probe 135 is positioned into the gas flow within the gas delivery conduit 100 in order to sample, measure and/or analyze the gas flow. The sensor probe 135 can include any type of sensor(s), such as, for example, a temperature sensor, thermistor, flow meter, oxygen ($O_2$), carbon dioxide ($CO_2$), nitric oxide and/or humidity sensor. The sensor probe 135 can be reusable or disposable and can be detachable or integrated with a conduit connector. The sensor probe 135 can be connected to a monitoring system having one or more processors for analyzing measurements and can communicate with the monitoring system via a cable or wirelessly. The monitoring system can include a display or other output device (e.g., speaker, alarm or wireless transmitter) for displaying measurements or generating an alarm. The sensor probe 135 and/or monitoring system can include a memory device such as, for example, an electrically erasable programmable read only memory (EEPROM), erasable programmable read only memory (EPROM), flash memory, non-volatile memory or the like. The sensor probe 135 can include a plurality of conductors for communicating signals to and from its components, including sensing component conductors and memory device conductors.

In some embodiments, the sensor port 130 is configured to accept different types of sensor probes 135, allowing sensor probes 135 to be changed based on the current use. For example, a humidity sensor can be used during humidity therapies while an oxygen sensor can be used during oxygen therapies.

In some embodiments, there may be only a single locking tab 151 or three or more locking tabs 151. In some embodiments, the alignment tabs 152 can be formed by multiple protrusions or discontinuous ridges rather than a single continuous protrusion. For example, two disconnected apexes 220 can be formed on opposite sides of the interior surface of the source conduit connector 125. In some embodiments, the source conduit connector 125 can include either alignment tabs 152 or locking tabs 151.

FIGS. 2B-2G illustrate various views of the source conduit connector 125 of FIG. 1C. This embodiment shares many of the structures and features discussed above with respect the source conduit connector 125 of FIG. 1A.

Figure 2B:
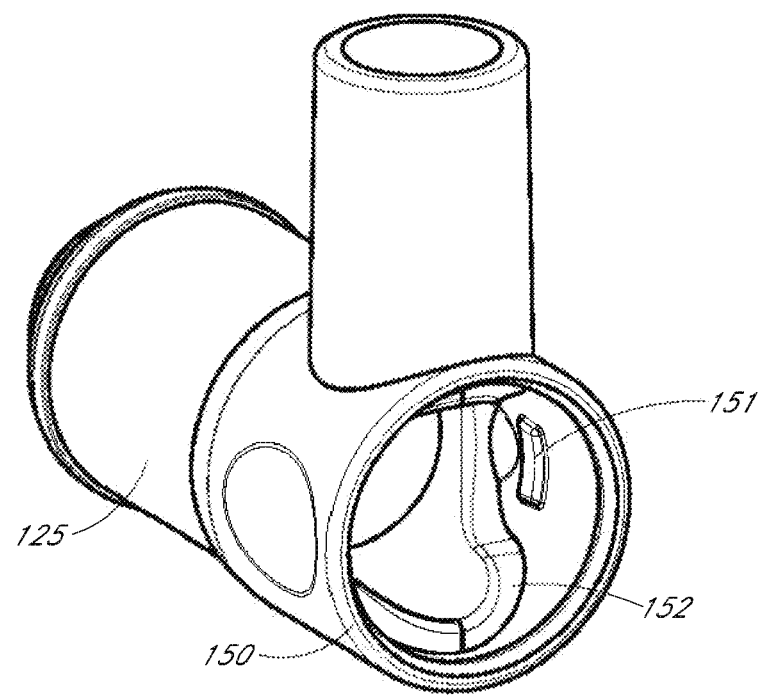
FIGS. 2B-2G illustrate various views of the source conduit connector of FIG. 1C.

FIG. 2B illustrates a perspective view of the source conduit connector 125 facing the terminal aperture 150 and showing, formed on the interior surface, a locking tab 151 and the alignment tab 152.

Figure 2C:
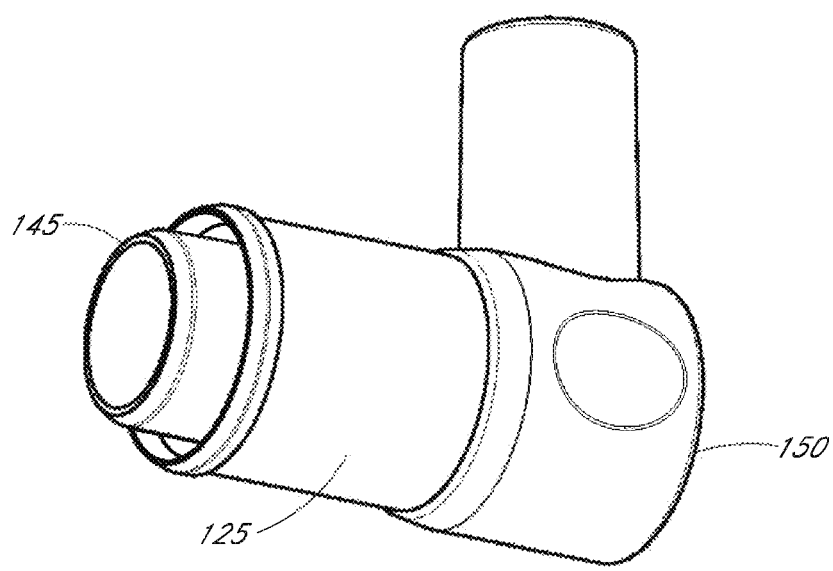

FIG. 2C illustrates a side perspective view of the source conduit connector 125 showing the source aperture 145.

Figure 2D:
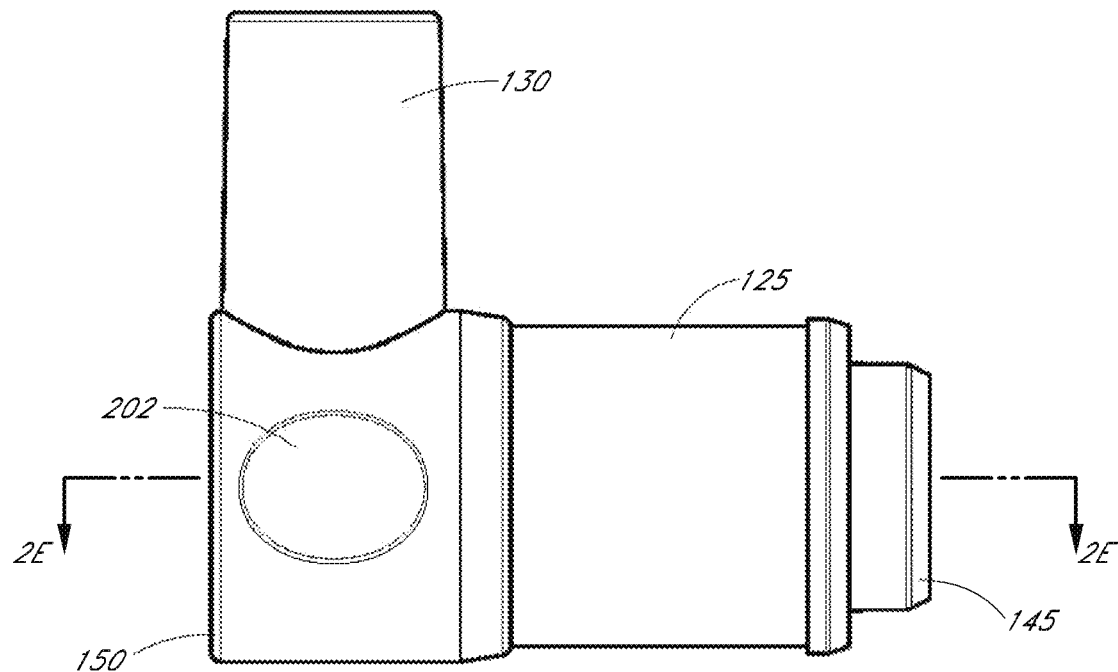

FIG. 2D illustrates a side view of the source conduit connector 125 showing the source aperture 145, the terminal aperture 150, a finger groove 202, and the sensor port 130.

Figure 2E:
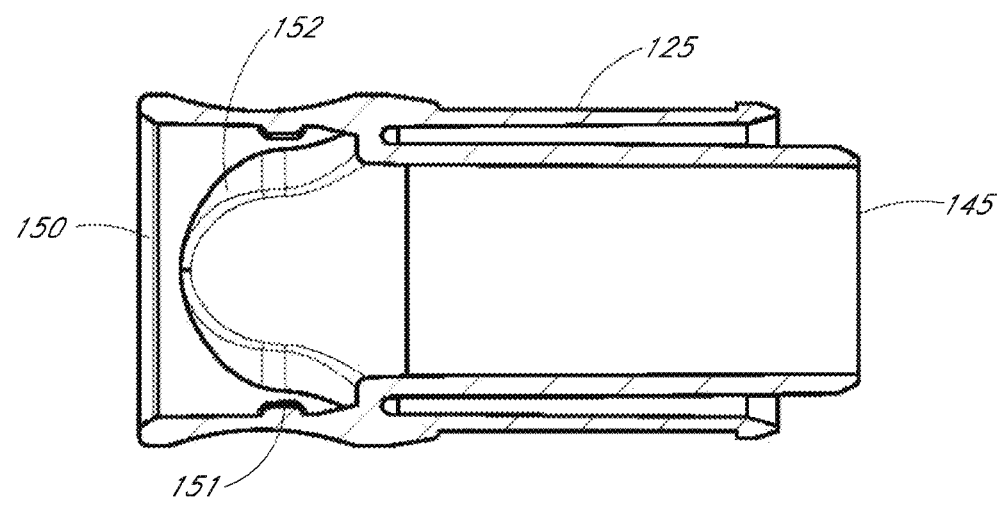

FIG. 2E illustrates a cross-sectional view of the source conduit connector 125 taken along the indicated line in FIG. 2D. FIG. 2E shows the source aperture 145, the terminal aperture 150 and, on the interior surface, the locking tabs 151 and the alignment tab 152.

Figure 2F:
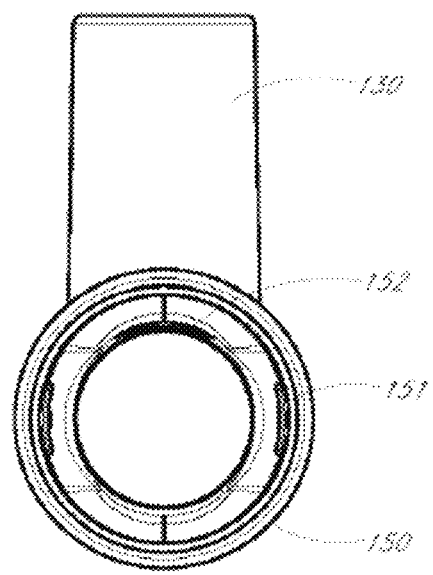

FIG. 2F illustrates a terminal aperture 150 facing view of the source conduit connector 125 showing the sensor port 130 and, on the interior surface, the locking tabs 151 and the alignment tab 152.

Figure 2G:
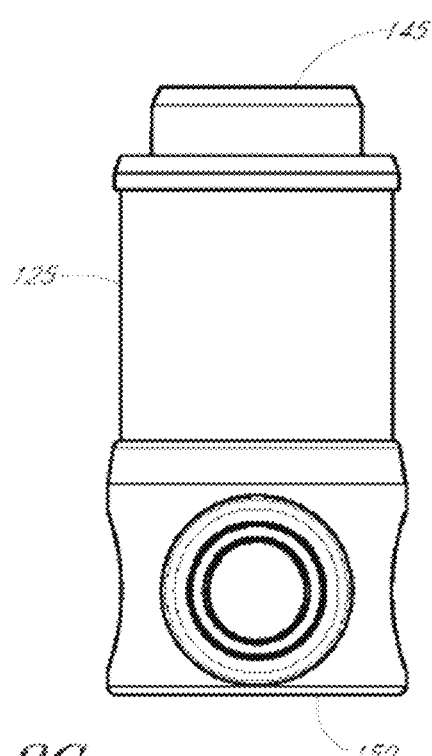

FIG. 2G illustrates a sensor port aperture facing view of the source conduit connector 125 showing the aperture of the sensor port 130 opening into the body of the source conduit connector 125. In FIG. 2G, the sensor port 130 is shown substantially adjacent and perpendicular to the terminal aperture 150, away from the source aperture 145.

FIGS. 3A and 3B illustrate perspective views of the connecting adapter 140 of FIG. 1A from a source aperture 305 side and a terminal aperture 310 side, respectively. In the illustrated embodiment, the connecting adapter 140 includes a substantially cylindrical tube having two locking fingers 153 extending from the source aperture 305. The locking fingers 153 can be spaced apart to form an insertion aperture 312 for the sensor probe 135 (FIG. 1A) to fit between the fingers 153. The insertion aperture 312 can provide an opening through which a portion of the sensor probe 135 extends into the gas delivery conduit 100, in order to sample airflow from within the gas delivery conduit 100 (FIG. 1A). The insertion aperture 312 can also allow the sensor probe 135 to be positioned closer to the nasal cannula 110 (FIG. 1A), for example, by allowing the connecting adapter 140 to extend around or over the sensor probe 135, towards the airflow source 115 (FIG. 1A). In one embodiment, the insertion aperture 312 allows the sensor probe 135 to be placed closer to the patient while simultaneously allowing a portion of the connecting adapter 140 to engage with the source conduit connector 125 (FIG. 1A). For example, without the insertion aperture 312, the sensor probe 135 may have to be placed past the ends 314 of the connecting adapter 140, further away from the nasal cannula 110, which can eliminate, inhibit or reduce some of the potential benefits discussed above for placing the sensor probe 135 closer to the patient.

In some embodiments, each locking finger 153 includes a locking recess 154 formed on the outer surface of the locking finger 153. In one embodiment, the locking recesses 154 are configured to lock with the locking tabs of the source conduit connector 125. In some embodiments, the locking fingers 153 include a flexible or semi-rigid material such that sufficient longitudinal force can cause the locking recesses 154 to pass over locking tabs 151 of the source conduit connector 125, thereby releasing the connecting adapter 140 from the source conduit connector 125. For example, pushing the connecting adapter 140 into the source conduit connector 125 (on assembly or connection) or pulling out the adapter 140 (on disconnection) can cause the locking tabs of the source conduit connector 125 to engage or disengage with the locking recesses 154 of the locking finger 153.

The connecting adapter 140 can include a locking channel 160 formed along the circumference of its external surface. In FIG. 3A, the edges of the channel are bounded by collars 320, 325 at the source and terminal apertures. Ridges, such as on the terminal conduit connector 120 (FIG. 1A), can lock into the channel 160. For example, pushing the connecting adapter 140 into the terminal conduit connector 120 (on assembly or connection) or pulling out the adapter 140 (on disconnection) can cause the ridges of the terminal conduit connector 120 to engage or disengage with the locking channel 160. The collars can prevent or inhibit disconnection of the ridges due to longitudinal force (e.g., force along the conduit 100 axis), while allowing the ridges to rotate along the locking channel 160. In some embodiments, the terminal collar 320 includes a flexible or semi-rigid material such that sufficient longitudinal force can cause the ridges to pass over the collar 320 and cause the connecting adapter 140 to release from the terminal conduit connector 120.

The connecting adapter 140 can have one or more optional spines 330 formed longitudinally on its interior surface. The spines 330 can provide rigidity to the connecting adapter and, in one embodiment, are spaced evenly along the interior circumference of the connecting adapter 140. In one embodiment, the spines 330 are tapered and can provide greater rigidity on one end compared to the other. For example, the source aperture 305 side of the connecting adapter 140 may need greater flexibility in order to attach and/or detach with the source conduit connector 125 and the spines 330 can taper (in height or width) towards the source aperture 305.

In some embodiments, the connecting adapter 140 can have one, two, three, four or more locking fingers 153 or spines 330. In some embodiments, other types of connection mechanisms can be used, such as, for example, a threaded mechanism, pinion mechanism, friction fit, circlip and/or adhesive or other chemical connector.

In some embodiments, different types of connecting adapters can be provided for connecting different types of conduit connectors. For example, a respirator conduit can have a different type of source conduit connector than a humidifier conduit. By changing the connecting adapter, the same nasal cannula can be connected to either the respirator conduit or the humidifier conduit. By providing interchangeable connecting adapters, the nasal cannula does not have to be changed, thereby minimizing patient discomfort by eliminating or reducing the need to replace the nasal cannula attached to the patient. Likewise, different types of terminal conduit connectors can be connected to the same type of source conduit connector by changing adapters. For example, the nasal cannula can be replaced with a face mask having a different terminal conduit connector type by attaching it to the same humidifier by using a different connecting adapter. The interchangeability of the connectors can potentially speed up the setup of gas delivery conduits, which can be particularly beneficial in emergency situations.

FIGS. 3C-3G illustrate various views of the connecting adapter 140 of FIG. 1C. This embodiment shares many of the structures and features discussed above with respect the connecting adapter 125 of FIG. 1A.

Figure 3C:
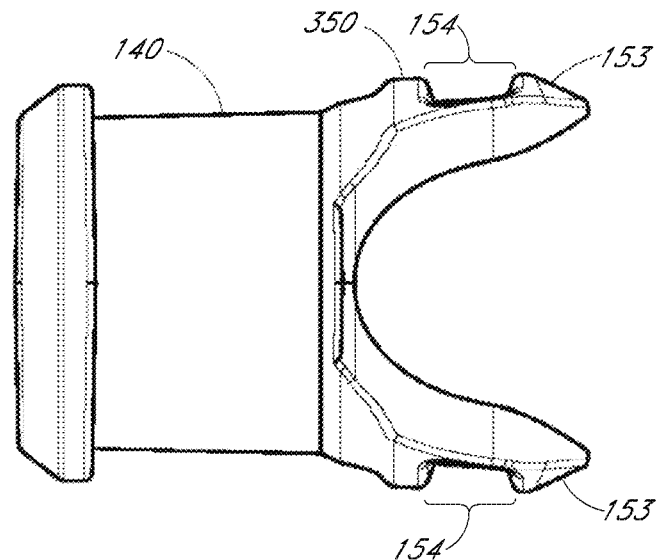
FIGS. 3C-3G illustrate various views of the connecting adapter of FIG. 1C.

FIG. 3C illustrates a top view of the connecting adapter 140 showing two locking fingers 153 extending from the body of the connecting adapter 140 and two locking recesses 154 formed on the exterior surface of the locking fingers 154. In some embodiments, raised strips 350 form the bottom boundary of the recesses 154 on the respective locking fingers 153. Each raised strip 350 can provide additional support and/or rigidity to each locking recess 350, allowing a more secure connection of the locking recesses with the corresponding locking tabs.

Figure 3D:
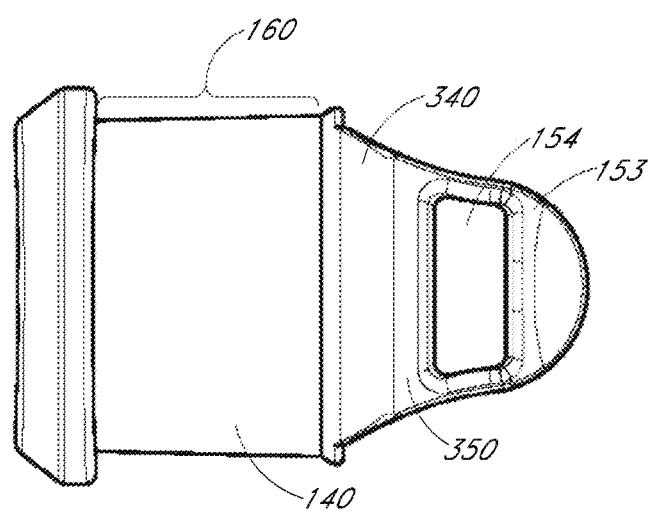

FIG. 3D illustrates a side view of the connecting adapter 140 showing a locking finger 153 extending from the body of the connecting adapter 140, a locking recess 154 formed on the exterior surface of the locking fingers, and the locking channel 160 formed along the circumference of the adapter's external surface. In the embodiment of FIG. 3D, the locking finger 153 widens from its end 314 to its base 340. By widening at its base, where the finger 153 connects with the body of the connecting adapter 140, the strength of the locking finger 153 is enhanced, making it more difficult to deform the locking finger 153 and disconnect it when it is engaged with the locking tab 151 of the source conduit connector 125. Additionally, the raised strip 350 can also enhance the strength of the locking finger 153.

Figure 3E:
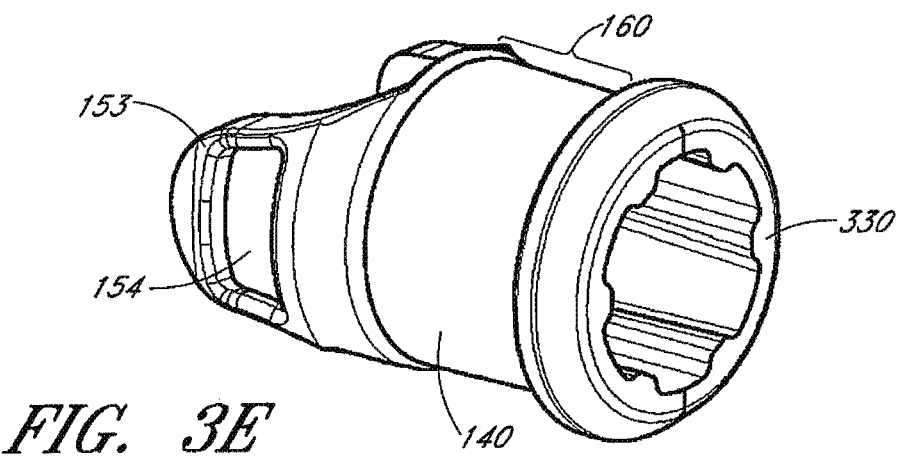

FIG. 3E illustrates a perspective view of the terminal conduit connector 120 facing aperture of the connecting adapter 140. FIG. 3E shows the locking finger 153, the locking recess 154, the locking channel 160 and the spines 330 formed longitudinally on the interior surface of the connecting adapter.

Figure 3F:
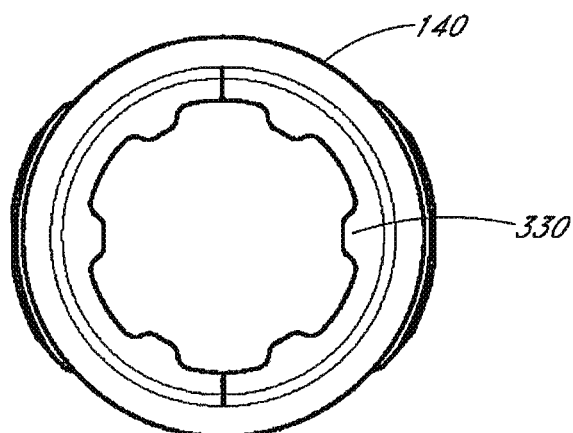
Figure 3G:
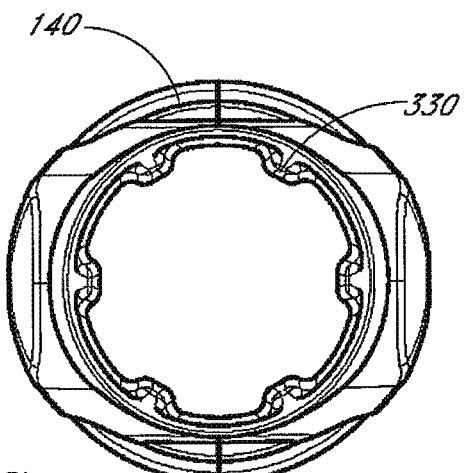

FIG. 3F illustrates a front facing view of an aperture of the connecting adapter 140 facing the terminal conduit connector 120. FIG. 3G illustrates a front facing view of an aperture of the connecting adapter 140 facing the source conduit connector 125. The spines 330 are shown formed on the interior surface of the adapter 130.

Figure 4A:
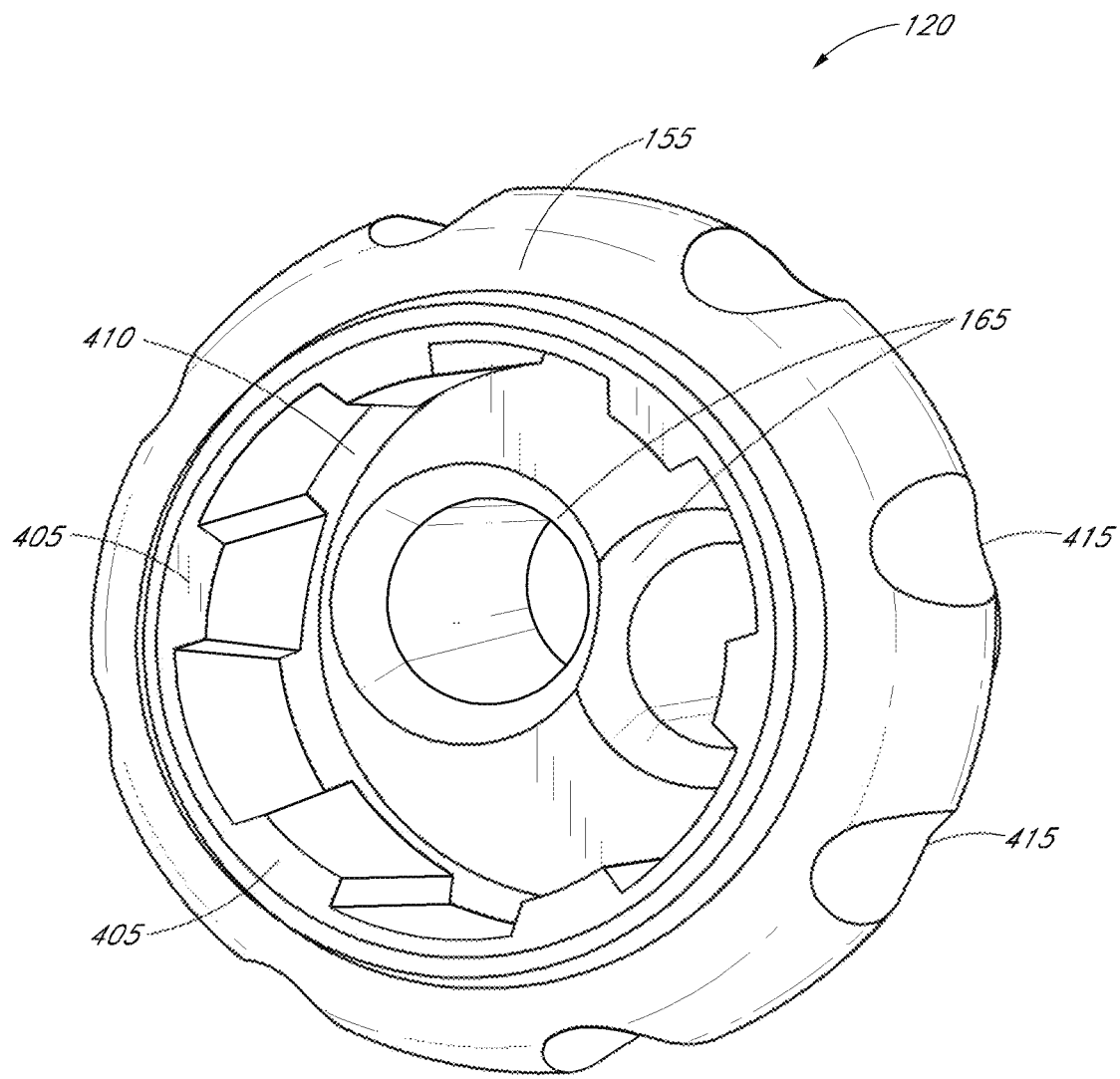
FIGS. 4A and 4B illustrate a perspective view of a source aperture side of the terminal conduit connector and a top view of the terminal conduit connector of FIG. 1A.
Figure 4B:
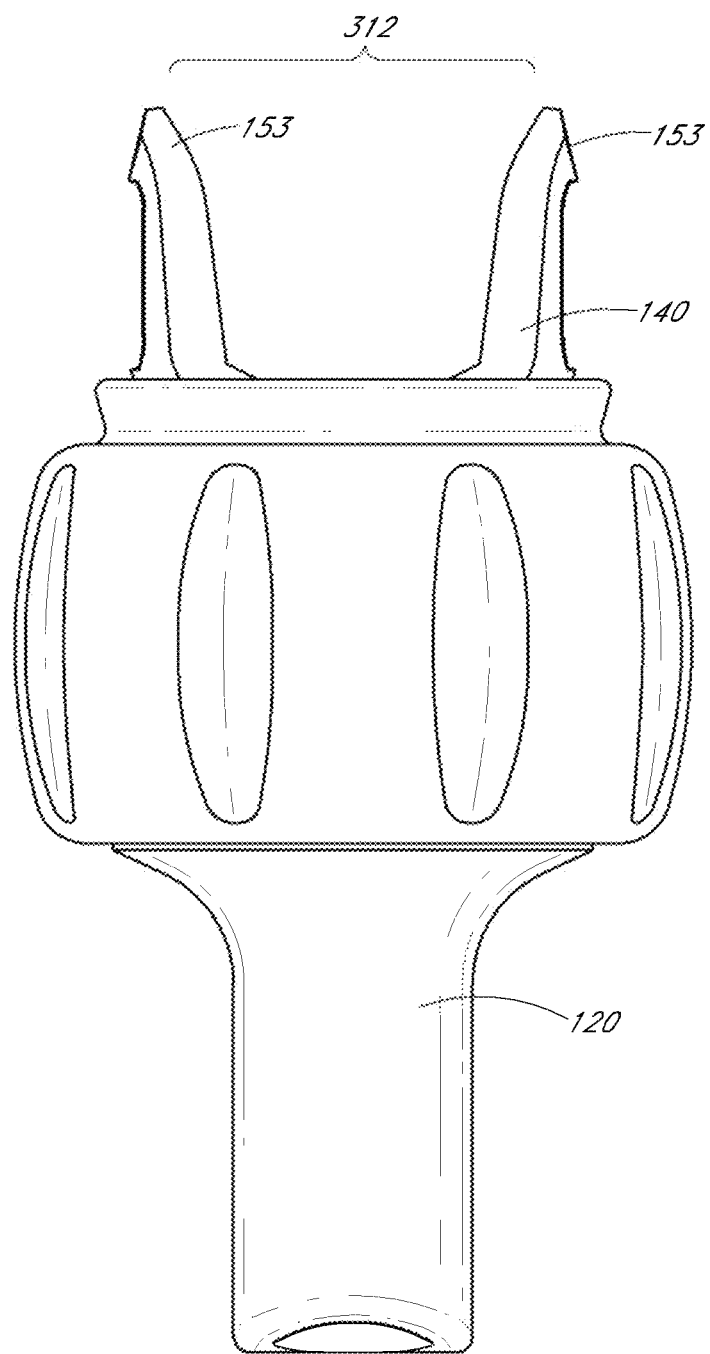

FIGS. 4A and 4B illustrate a perspective view of the source aperture 155 side of the terminal conduit connector 120 and a top view of the terminal conduit connector 120 of FIG. 1A. FIG. 4A illustrates the terminal conduit connector 120 without the connecting adapter 140 inserted, while FIG. 4B illustrates the terminal conduit connector 120 with the connecting adapter 140. In the illustrated embodiment, the terminal conduit connector 120 includes ridges 405 spaced along the circumference of the interior surface of the terminal conduit connector 120. In one embodiment, the ridges 405 are protrusions or tabs formed longitudinally by surrounding cutouts, or axially, along the terminal conduit connector 120. The ridges 405 and surrounding cutouts can decrease frictional engagement with the connecting adapter 140, thereby improving rotatability. The ridges 405 can be tapered, in width or in height. The tapering can allow insertion of the connecting adapter 140 to be accomplished with less force while requiring more force for removing the connecting adapter 140 as a larger surface area of each locking tab engages with the terminal collar 320 (FIG. 3A) of the connecting adapter 140. In one embodiment, a locking groove 410 is formed along the circumference of the terminal conduit connector 120 and is configured to engage with the terminal collar 320 of the connecting adapter 140, thereby increasing the longitudinal force needed to disengage the terminal conduit connector 120 from the connecting adapter 140.

In one embodiment, the terminal conduit connector 120 includes a terminal aperture 165 on the terminal conduit connector 120 configured to receive a cannula tube of a nasal cannula 110 (FIG. 1A). The terminal aperture 165 can include two openings for receiving a double conduit cannula tube, wherein each conduit connects, on the opposite end of the tube, to a prong for insertion into a patient's nostril. In the illustrated embodiment, the openings are optionally surrounded by an angled surface configured to funnel airflow into the double conduit cannula tube, which can improve airflow. The terminal conduit connector 120 can also include one or more finger grooves 415 formed on the outside surface of the terminal conduit connector 120 in order to provide additional purchase or friction to a user, for example, for connecting or disconnecting the connector 105 (FIG. 1A) components. In FIG. 4A, multiple finger grooves 415 are spaced along the outside circumference of the terminal conduit connector 120.

Other configurations of the terminal conduit connector 120 are possible. For example, in some embodiments, the locking tab 405 is a single, continuous ridge. In other embodiments, the ridges 405 are formed perpendicular or angled relative to the axis of the terminal conduit connector 120. In some embodiments, the locking groove 410 is not included. The aperture 165 can be a single opening. For example, the aperture 165 can be configured to receive a single conduit to a face mask.

FIGS. 4C-4G illustrate various views of the terminal conduit connector 120 of FIG. 1C. This embodiment shares many of the structures and features discussed above with respect the terminal conduit connector 120 of FIG. 1A.

Figure 4C:
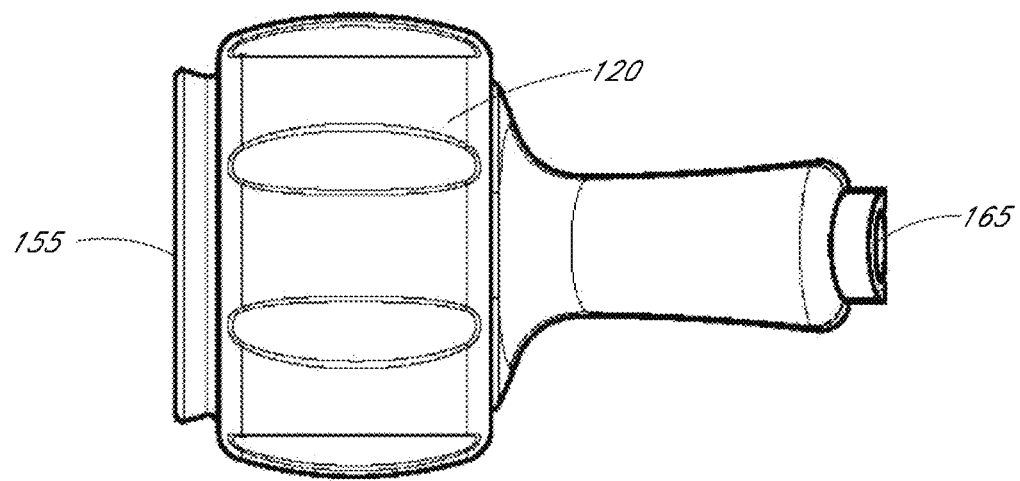
FIGS. 4C-4G illustrate various views of the terminal conduit connector of FIG. 1C.

FIG. 4C illustrates a side view of the terminal conduit connector 120 showing the terminal apertures 165 for receiving nasal cannula and the source aperture 155. A first portion of the body of the terminal conduit connector 120 that receives the connecting adapter 140 is a first height. A second portion of the body of the terminal conduit connecter 120 that receives the nasal cannula is a second, lower height.

Figure 4D:
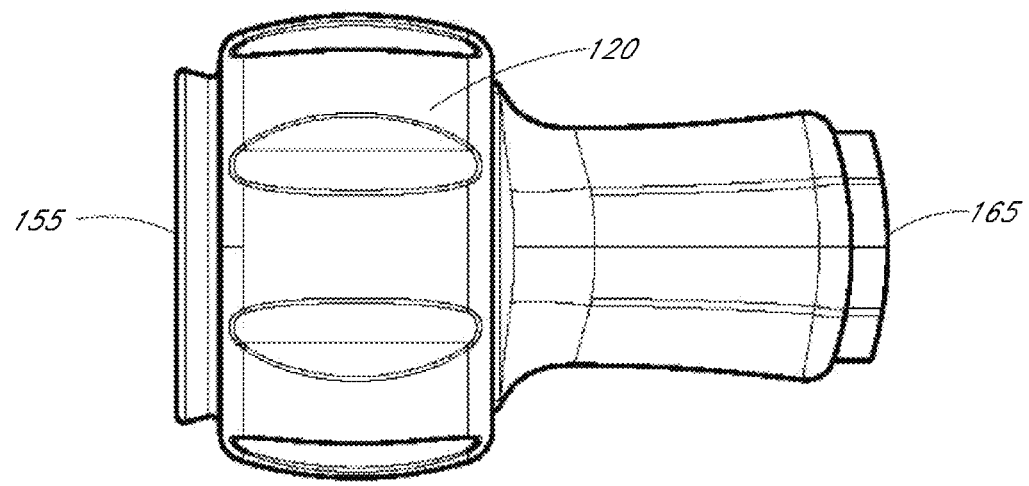

FIG. 4D illustrates a top down view of the terminal conduit connector 120 showing the terminal apertures 165 and the source aperture 155. The first portion of the body of the terminal conduit connector 120 has a first width while the second portion of the body has a second, narrower width.

Figure 4E:
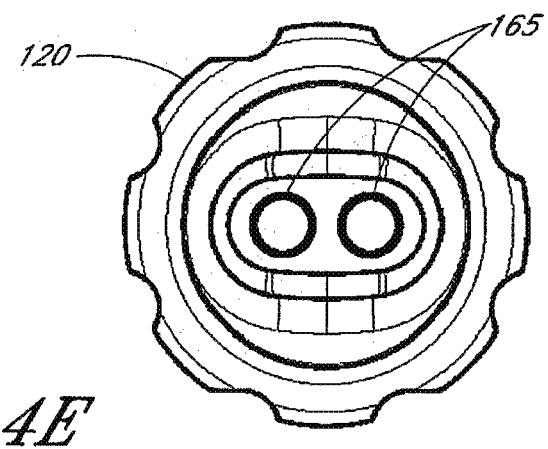
Figure 4F:
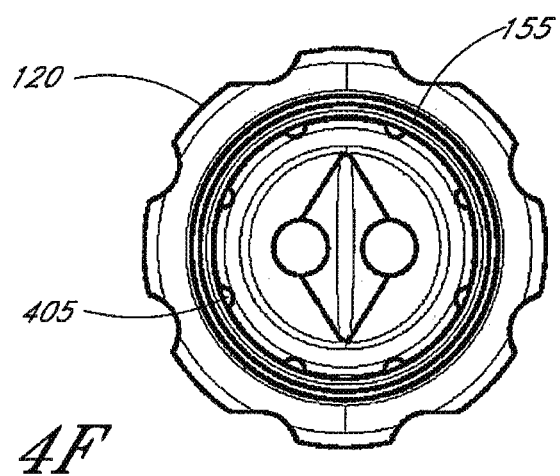
Figure 4G:
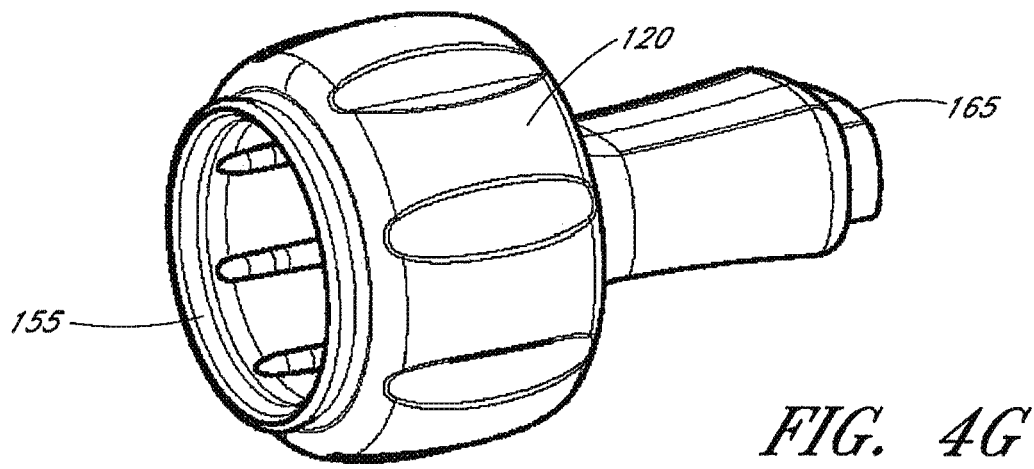

FIG. 4E illustrates a facing view of the terminal apertures 165. FIG. 4F illustrates a facing view of the source aperture 155 that shows the ridges 405 spaced along the circumference of the interior surface of the terminal conduit connector 120.

Figure 5A:
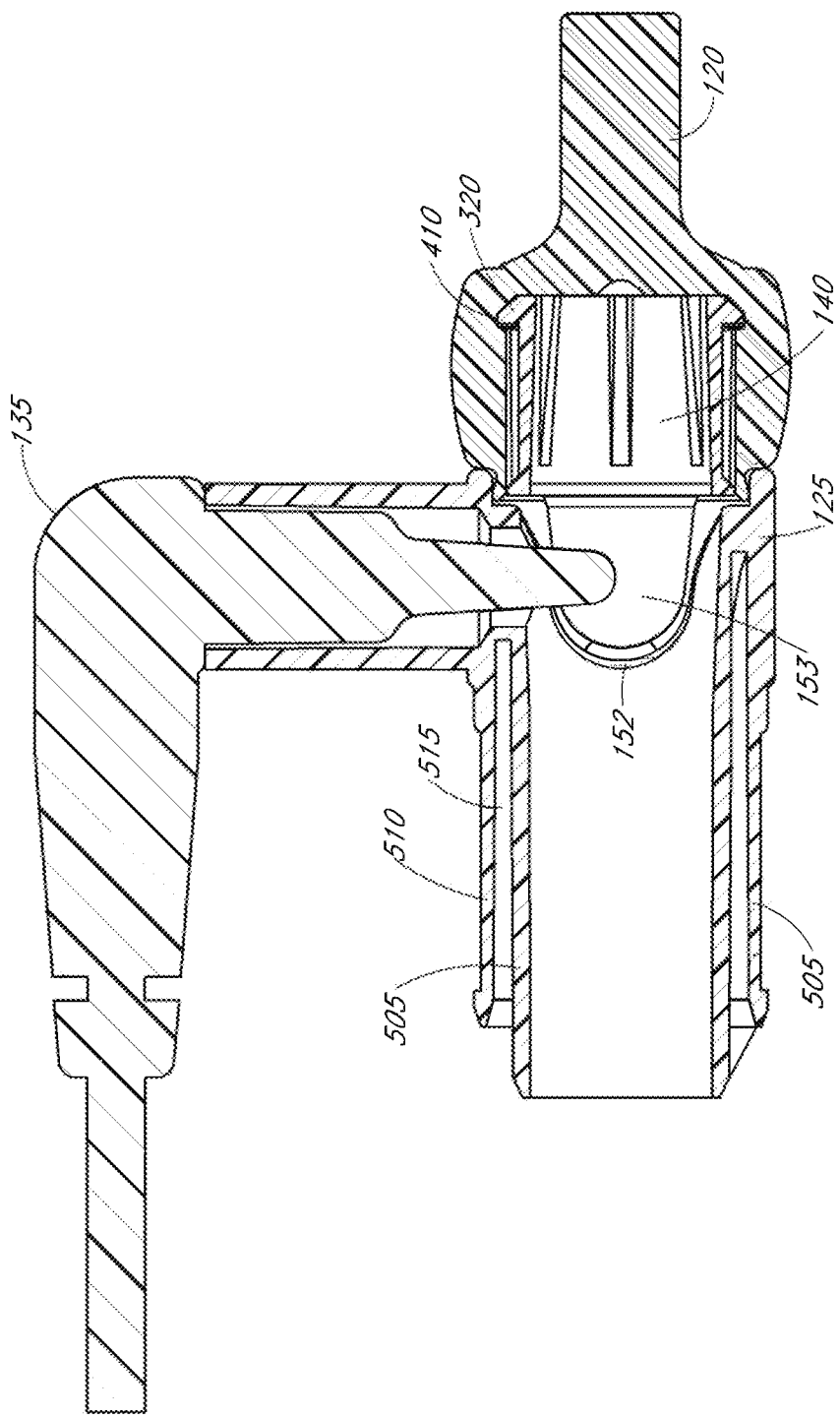
FIGS. 5A-C illustrate a longitudinal cross-sectional view of the connector of FIG. 1A.
Figure 5B:
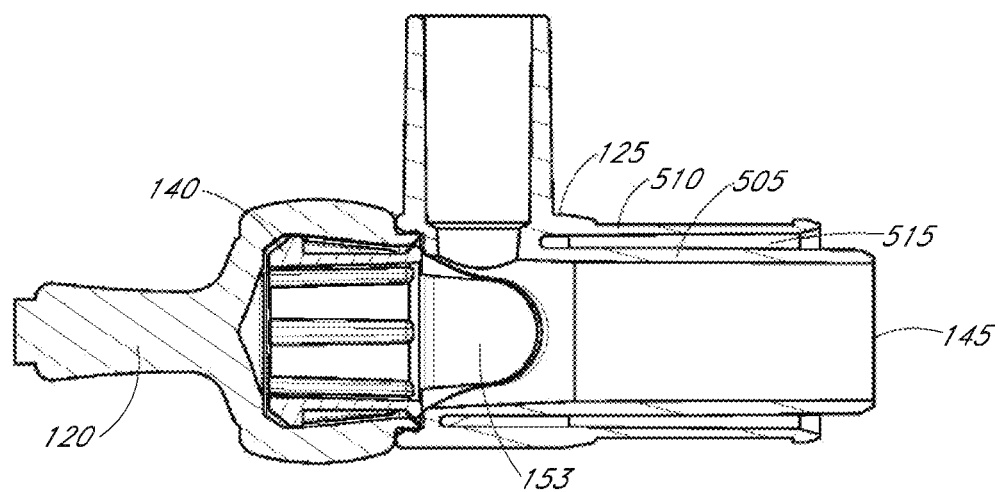
Figure 5C:
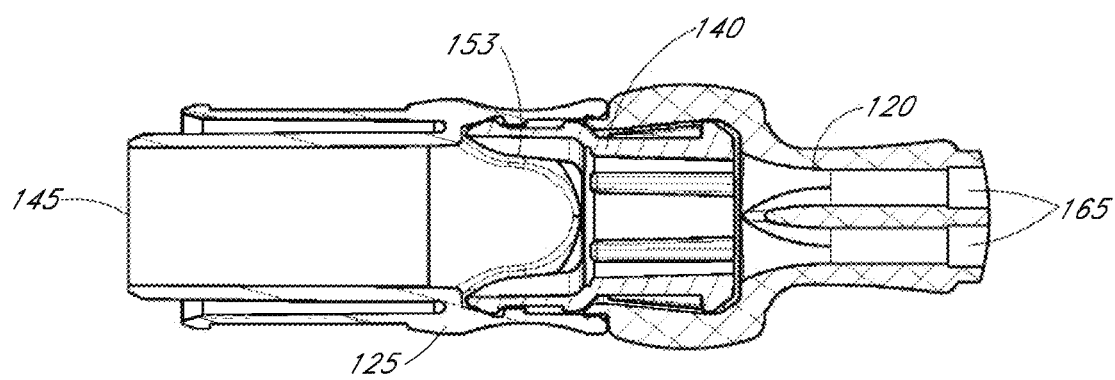

FIGS. 5A-C illustrate a longitudinal cross-sectional view of the connector 105 embodiment of FIG. 1A. FIGS. 5A-C illustrate the terminal collar 320 of the connecting adapter 140 engaged with the locking groove 410 of the terminal conduit connector 120. A portion of the sensor probe 135 fits between the fingers 153 of the connecting adapter. FIGS. 5A-C illustrate the fingers 153 fitting against the alignment tabs 152. In one embodiment, the source conduit connector 125 includes an inner cylinder 505 within an outer cylinder 510, forming an insertion groove 515 for receiving the delivery tube 115 (FIG. 1A). In one embodiment, pressure from the inner and outer cylinders maintains a pressure fit with the delivery tube 115, keeping the delivery tube 115 connected to the source conduit connector 125.

FIG. 6 illustrates a cross-section taken along an axis 167 of FIG. 1B facing towards the nasal cannula 110 (FIG. 1A) and illustrates the engagement of the connecting adapter 140 with the source conduit connector 125. In the illustrated embodiment, the source conduit connector 125 and terminal conduit connector 120 are attached via the connecting adapter 140. The locking tabs 151 formed on the interior surface of the source conduit connector 125 engage with the recesses 154 on the fingers 153 of the connecting adapter 140. The engagement inhibits longitudinal movement of the adapter and limits accidental disengagement of the connector 105 (FIG. 1A). The alignment tabs 152 can guide the fingers 153 into position for engagement.

As illustrated in FIG. 6, the sensor port 130 provides the sensor probe 135 with access to the airflow within the gas delivery conduit 100 (FIG. 1A). Airflow from the airflow source passes by the sensor probe 135 before exiting through the terminal aperture 165 of the terminal conduit connector 120.

As will be apparent, there are many possible embodiments for the connector 105. For example, in some embodiments, the connector 105 does not include a connecting adapter 140 or another component. In some embodiments, elements, such as tabs, protrusions, recesses, channels or grooves, are located on different components. For example, while the above disclosure describes a first element of a connecting mechanism (e.g., protrusion or tab) to be located on a first component while a second element of the connecting mechanism (e.g., recess, channel or groove) is located on a second component, in some embodiments, the locations of the elements can be switched, with the first element on the second component and the second element on the first component. In some embodiments, certain elements may not be included. In one embodiment, a first connector component can be configured to attach over a second connector component while in another embodiment, the second connector component can be configured to attach over the first connector component.

In some embodiments, different types of connections can be used to attach the components of the connector 105. For example, adhesives or other chemical agents may be used to permanently affix some components together. In other examples, different mechanical connection mechanisms can be used, such as a snap fit, thread, friction fit or circlip. The components of the connector 105 can be composed of various types of flexible, semi-rigid, or rigid materials. For example, the connecting adapter 140 and source conduit connector 125 can include polypropylene materials and the terminal conduit connector 120 can include of THERMOLAST materials. Other materials such as plastics, thermoplastics, silicone, glass-filled nylon, metal, spring steel, polycarbonate, PVC, polyethylene, rubber (e.g., natural or vulcanized), polyurethane, or the like can be used. For example, in one embodiment, the connecting adapter 140 includes ABS plastic, the source conduit connecter 125 includes polypropylene, and/or the terminal conduit connector 120 includes thermoplastic elastomer.

In some embodiments, some of the releasable connection mechanisms can be stronger than others. In one embodiment, the connection formed by the connecting adapter 140 with the source conduit connector 125 is weaker than the connection formed by the connecting adapter 140 with the terminal conduit connector 120. Thus, pulling apart the conduit connectors 120, 125 can cause the connecting adapter 140 to separate from the source conduit connector 125 while remaining connected to the terminal conduit connector 120. This configuration can facilitate changing patient interfaces by allowing another patient interface to be easily or quickly attached to the source conduit connector 125. Other configurations are possible, for example, the connecting adapter 140 can be configured to remain connected with the source connecting conduit 125.

In some embodiments, the connections of the connector 105 are configured to allow a quick connect or quick release of the connector 105 components. For example, the components can be configured to connect or release with a single motion (e.g., when pushed together or pulled apart). The components can be configured to self-align during engagement, such that the connecting mechanisms of the components align automatically. In another example, the connections of the connector 105 with the gas delivery tube 115 (FIG. 1A) and/or the nasal cannula 110 can be stronger relative to other connections (e.g., the connections with the connecting adapter 140), such that longitudinal force applied to the gas delivery conduit 100 causes those other, weaker connections to disconnect first. In some embodiments, the connections with the gas delivery tube 115 and/or the nasal cannula 110 are permanent or semi-permanent, in order to eliminate or reduce accidental disconnections.

Other embodiments of the connector 105 are possible. In some embodiments, the terminal aperture 165 includes a single opening, two openings, or three or more openings. There can be one, two, or more than two finger grooves 415 (FIG. 4A) on the outside. In some embodiments, the gas delivery conduit 100 or portions of the conduit can be attached to the patient via a lanyard (e.g., around the patient's neck), clip, or other fastening mechanism. The seals formed by the components can be air-tight or can allow some air to leak. In some embodiments, components of the connector 105 can be colored differently to indicate a size of the connector. For example, red can indicate adult sized connectors while blue can indicate infant connectors. In some embodiments, the gas deliver conduit 100 can include one or more spring tube sections, which can increase flexibility.

The components of the connector 105 can be formed in various sizes, depending on its intended use. For example, connectors for gas delivery conduits 100 for children or infants can be smaller than connectors for gas delivery conduits 100 for adults. In some embodiments, the source conduit connector 125 has an outer diameter in the range of 5-30 mm, though this diameter may be larger or smaller in other embodiments. In one embodiment, the outer diameter is about 15 mm. The other connector components 105 can be sized correspondingly to the source conduit connector 125. For example, the other components may be sized approximately the same as the source conduit connector 125 in order to engage with it.

Figure 7:
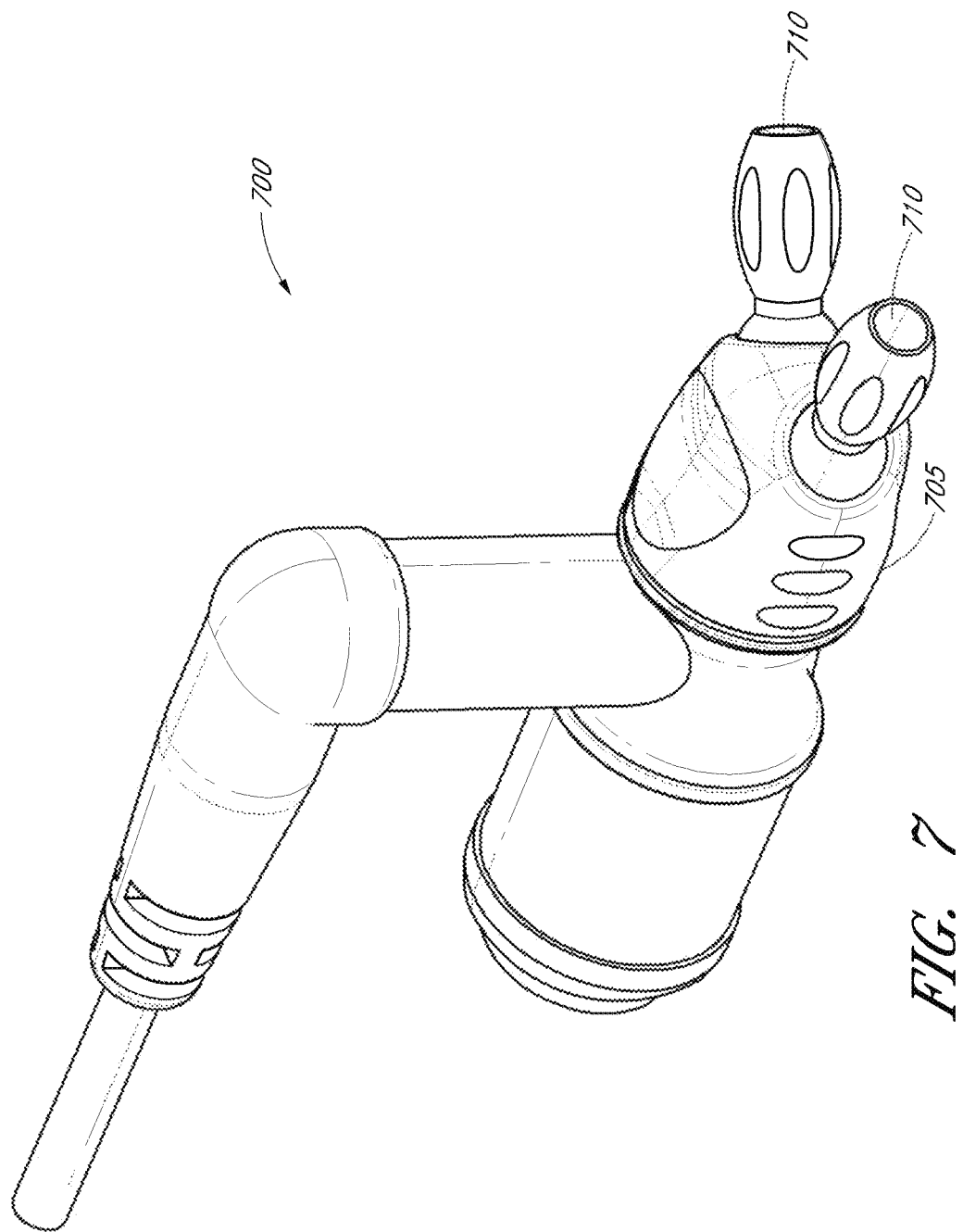

FIG. 7 illustrates an alternate connector embodiment 700 of the connector of FIG. 1A. In FIG. 7, the terminal conduit connector 705 includes dual ball and socket connections 710 for individually connecting cannula tubes to the terminal conduit connector. The ball and socket connections 710 can be moved independently of each other. This can allow the cannula tubes to be untwisted or untangled separately, thereby facilitating adjustment of the nasal cannula. In addition, while longer cannula tubes generally allow a greater degree of adjustments of the nasal cannula, the greater freedom of movement provided by the ball and socket connections 710 can potentially provide similar degrees of adjustments while allowing cannula tubes of shorter length to be used.

Figure 8:
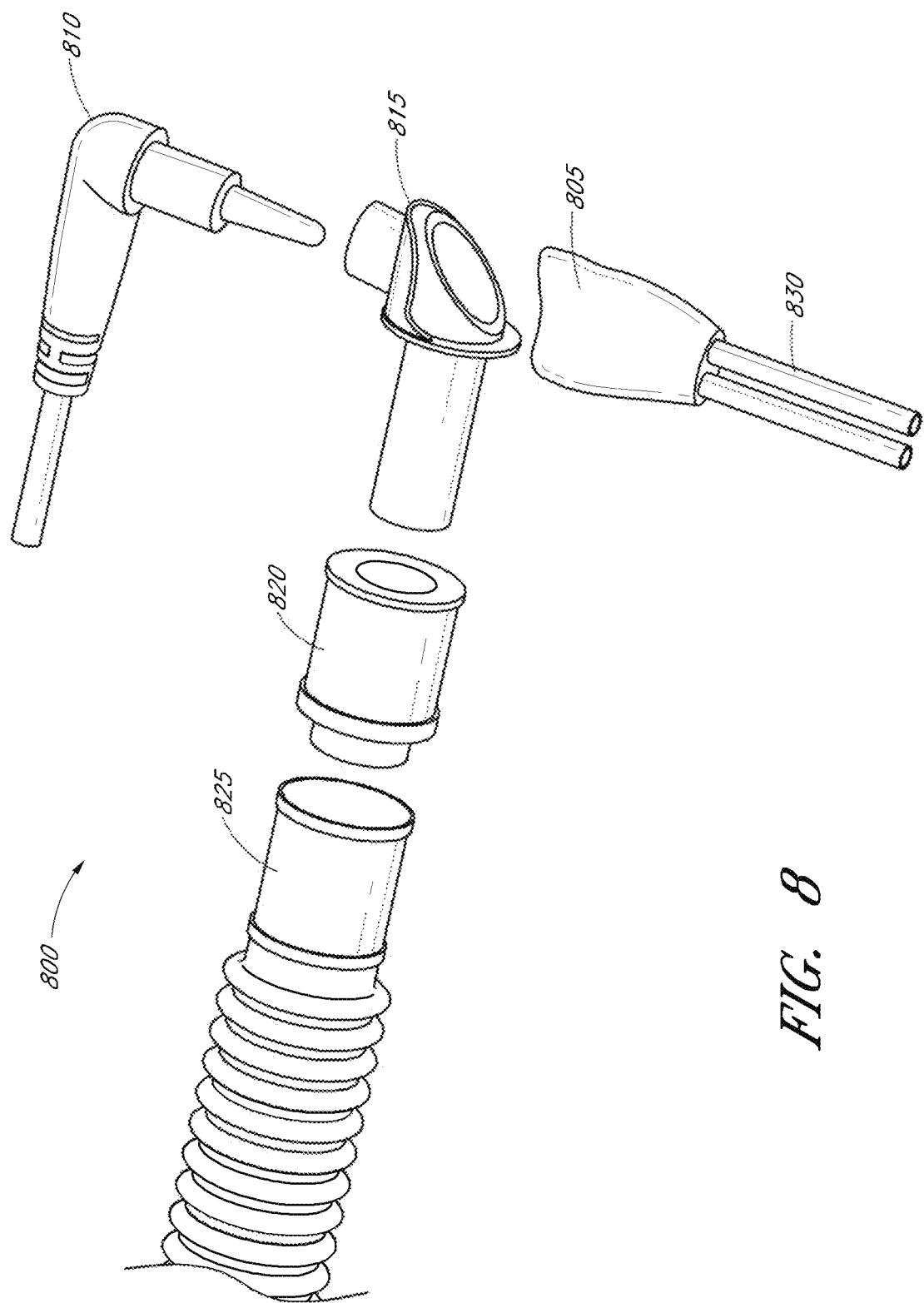

FIG. 8 illustrates another alternate connector embodiment 800 of the connector of FIG. 1A. In FIG. 8, the terminal conduit connector 805 and sensor probe 810 connects substantially perpendicularly to the source conduit connector 815. The source conduit connector 815 connects to a swivel tube 820 that in turn connects to a gas delivery tube 825. As the sensor probe, terminal conduit connector and source conduit connector are rotatably attached to the gas delivery tube via the swivel tube 820, the connector can be laid flat on a patient's bed, potentially increasing patient comfort or keeping the connector out of the way. In the illustrated embodiment, the connector 800 is shaped to form a substantially 90 degree angle, thereby redirecting airflow over the sensor probe 810 and into the nasal cannula 830. This redirection of the airflow can advantageously allow the sensor probe 810 to detect disconnection of the terminal conduit connector 805 by detecting a change in the airflow. For example, the sensor probe 810 can detect a change in the direction, speed or compositions (e.g., humidity or temperature) of the airflow and determine that the terminal conduit connector 805 is no longer attached to redirect the airflow.

Figure 9:
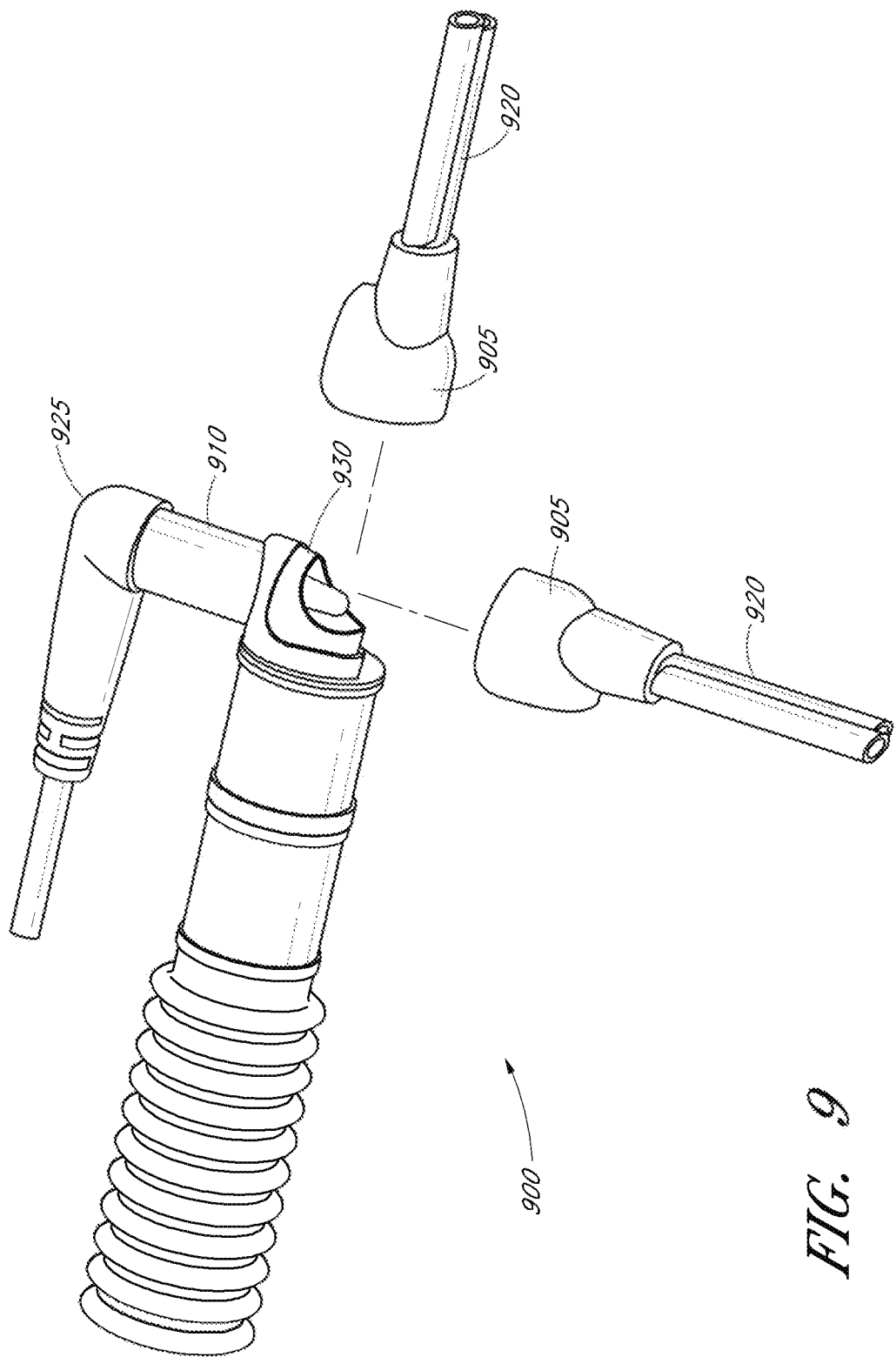

FIG. 9 illustrates another alternate connector embodiment 900 of the connector of FIG. 1A. In FIG. 9, the terminal conduit connector 905 can connect either substantially perpendicularly or substantially straight with the source conduit connector 910. The dual orientation of the terminal conduit connector 905 can provide greater flexibility in adjusting the nasal cannula 920.

The source conduit connector 910 can include an aperture 930 through which the sensor probe 925 can partially extend into the terminal conduit connector 910, thus placing the sensor probe 925 closer to the entry point of the airflow into the cannula. In the illustrated embodiment, the aperture 930 is notched to allow the sensor probe 925 to extend past the aperture 930. This can allow the sensor probe 925 to gather more accurate measurements of the temperature, humidity or other parameter of the gases inhaled by the patient.

FIG. 10 illustrates another alternate connector embodiment 1000 of the connector of FIG. 1A. In FIG. 10, a terminal conduit connector 1005 connects to a connecting adapter 1010, which connects to a source conduit connector 1015. The connecting adapter 1010 includes a collar 1020 having a greater diameter than the adjacent terminal conduit connector and source conduit connector. Thus, when the connector is assembled, a portion of the collar 1020 extends past the outer housing of the connected terminal conduit connector and source conduit connector and remains visible as a ring. The collar 1020 can be colored to indicate sizing information for the connector 1000. The collar 1020 can also provide a better friction hold to a user, thereby allowing a shorter connector to provide similar amount of frictional grip, which can facilitate the attachment and/or detachment of the connector components.

Figure 11A:
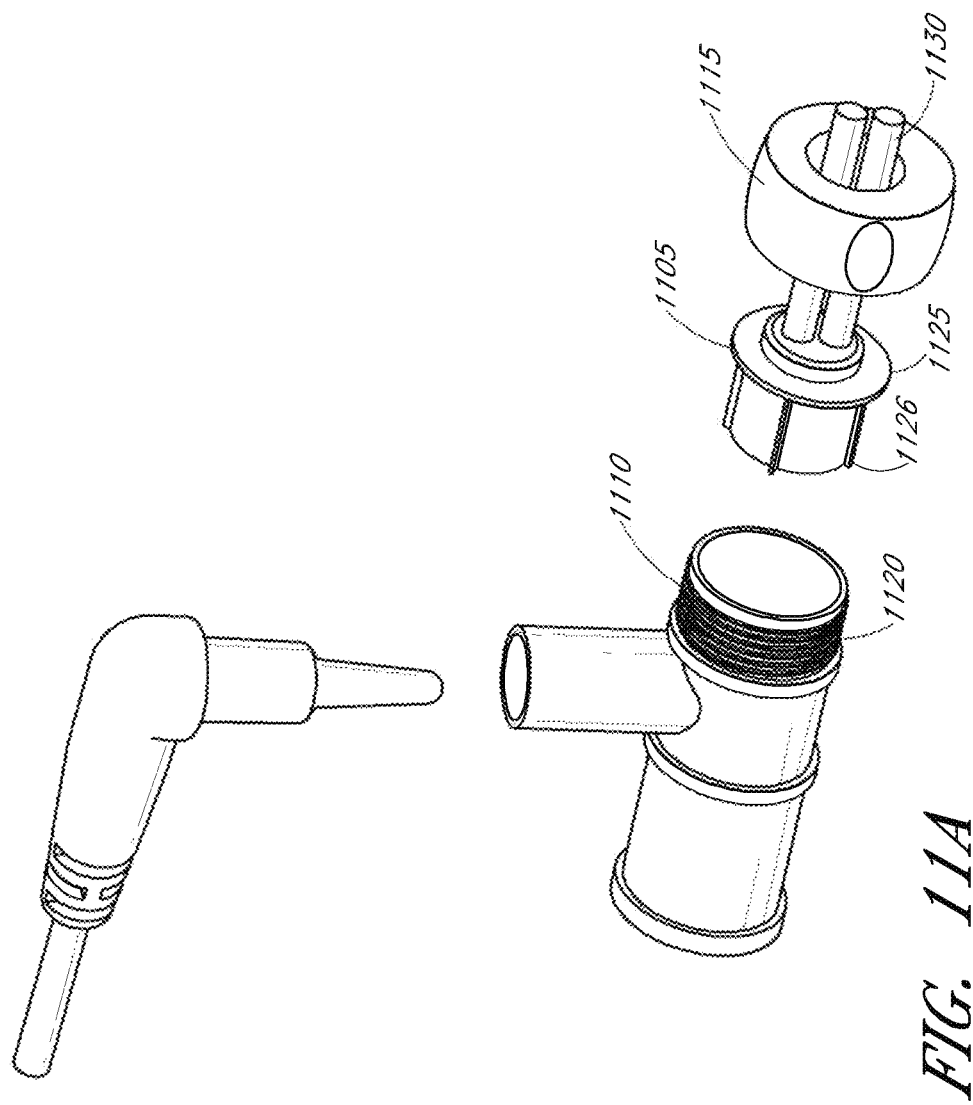
Figure 11B:
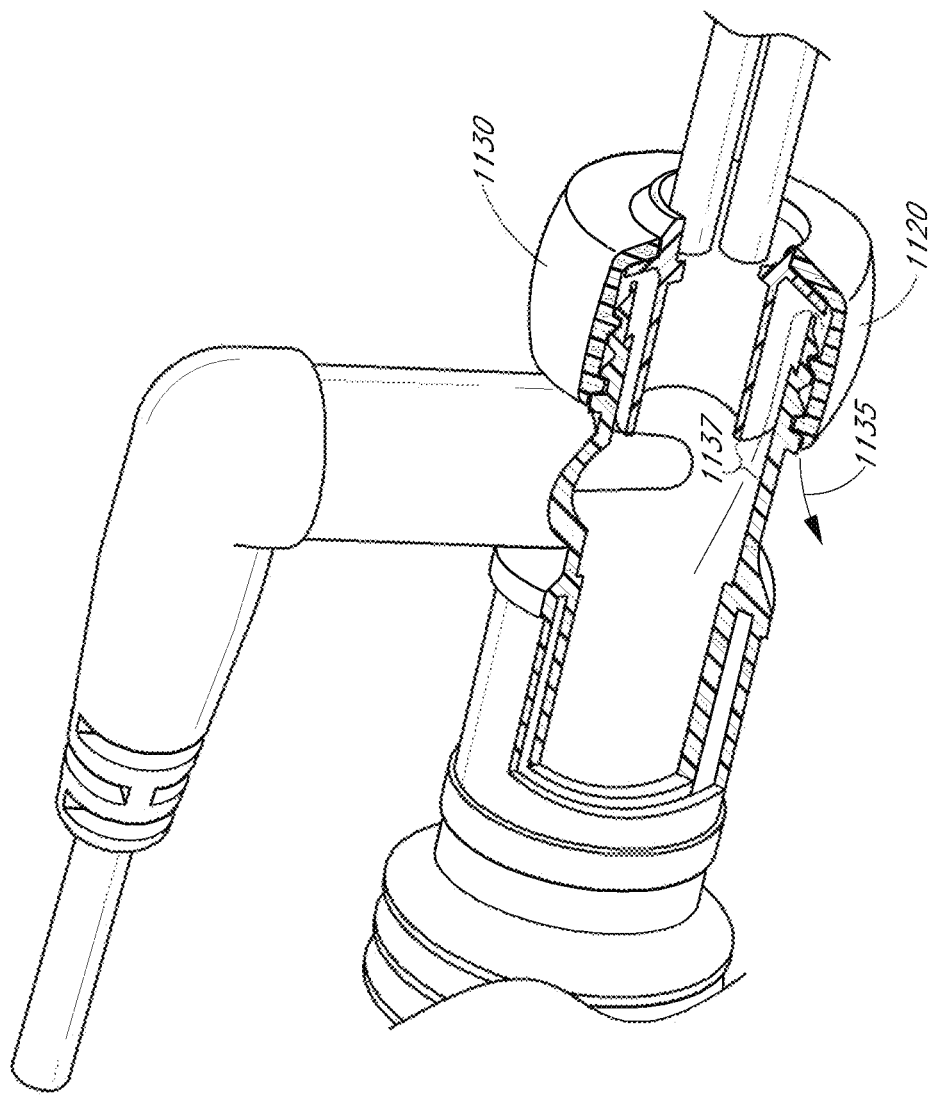

FIG. 11A and FIG. 11B illustrate another alternate connector embodiment 1100 of the connector of FIG. 1A. In FIG. 11, a terminal conduit connector 1105 fits within a source conduit connector 1110, while a threaded cap 1115 fits over the terminal conduit connector 1105 and engages with a threaded end 1120 of the source conduit connector. The threaded cap 1115 engages with a collar of the terminal conduit connector 1125 and keeps the terminal conduit connector pressed against the source conduit connector. Fins 1126 formed on the body of the terminal conduit connector 1105 can provide a space between the exterior of the terminal conduit connector 1105 and the interior of the source conduit connector 1110.

In one embodiment, the threaded cap 1115 only engages with some of the thread flutes on the threaded end 1120 of the source conduit connector. For example, if the threaded end 1120 has six thread flutes, the thread cap 1115 is configured to engage with only three of the flutes, leaving the other three thread flutes vacant. The partial engagement of the threads can allow condensate collecting in the connector to escape out along the vacant threads, along an outflow path 1135, thereby preventing or inhibiting condensate from entering the cannula 1130. The outflow path 1135 or venting channel can be partly formed by the space 1137 between the exterior of the terminal conduit connector 1105 and the interior of the source conduit connector 1110.

Figure 12:
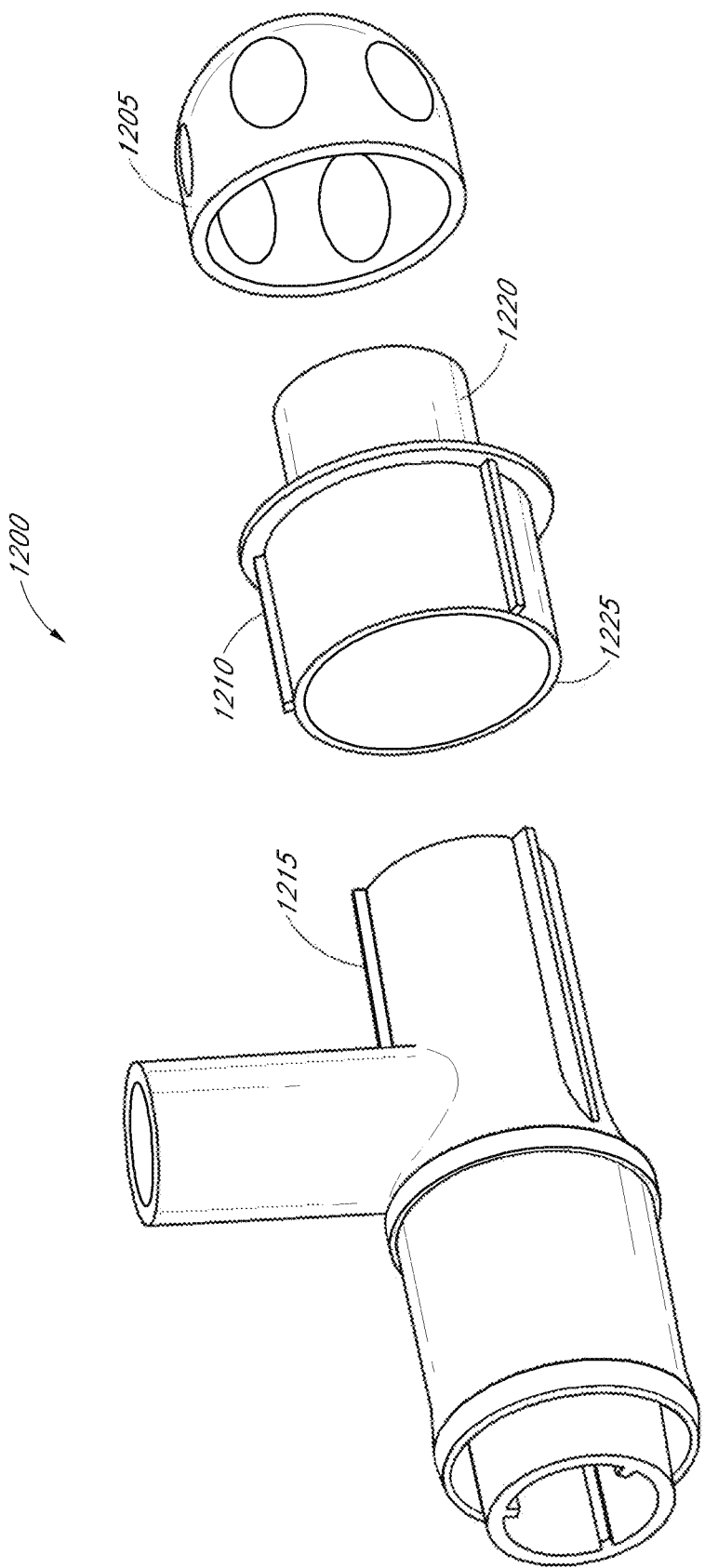

FIG. 12 illustrates another alternate connector embodiment 1200 of the connector of FIG. 1A. In FIG. 12, a terminal conduit connector 1205 connects to a connecting adapter 1210, which connects to a source conduit connector 1215. The connecting adapter includes an end 1220 for connecting with the terminal conduit connector 1205, for example, via threads or friction fit. The source aperture 1225 of the connecting adapter 1210 fits over the source conduit connector 1215.

Figure 13:
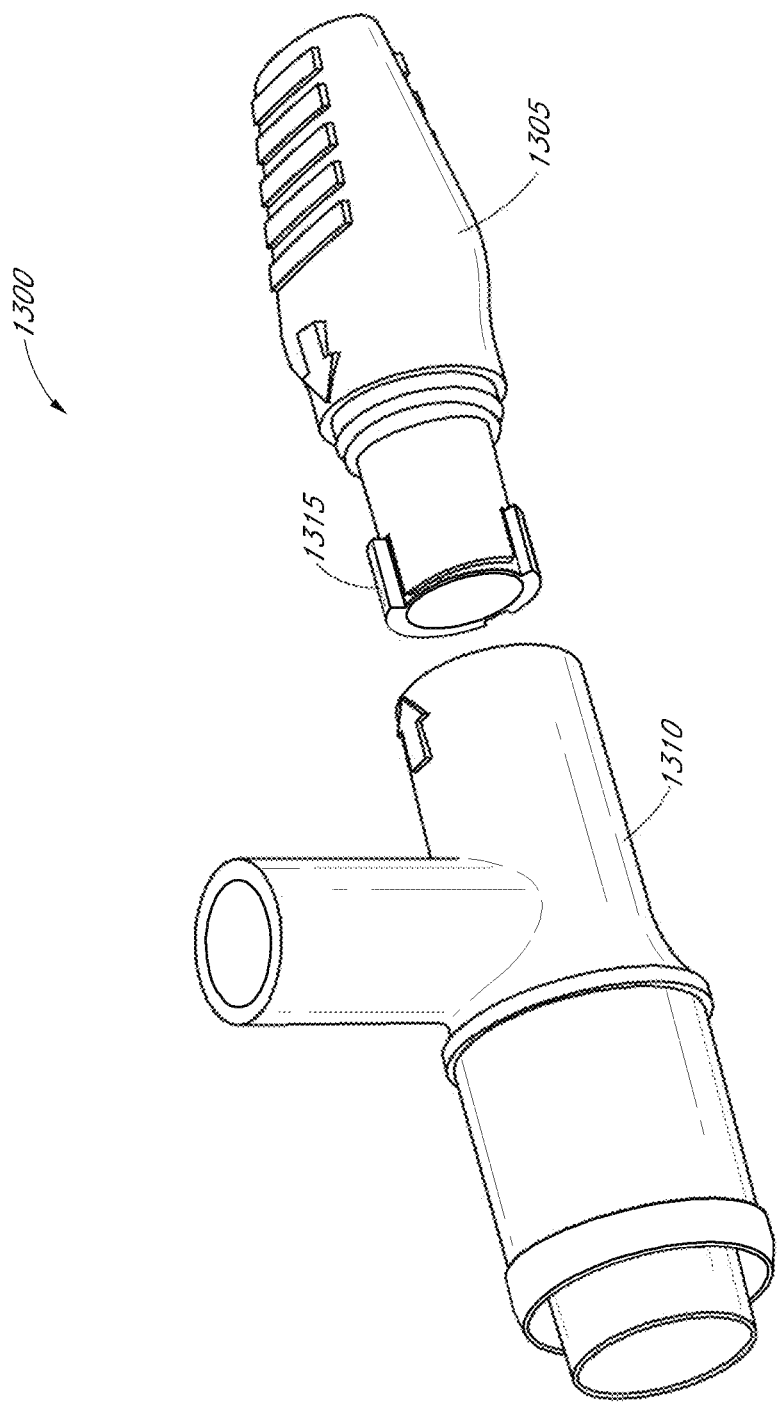

FIG. 13 illustrates another alternate connector embodiment 1300 of the connector of FIG. 1A. In FIG. 13, a terminal conduit connector 1305 connects to a source conduit connector 1310. Locking tabs 1315 formed on a connecting end of the terminal conduit connector engage with other locking tabs within the source conduit connector 1310. Twisting the terminal conduit connector 1305 relative to the source conduit connector 1310 can cause the locking tabs 1315 to disengage, allowing the connector 1300 to be separated.

Figure 14:
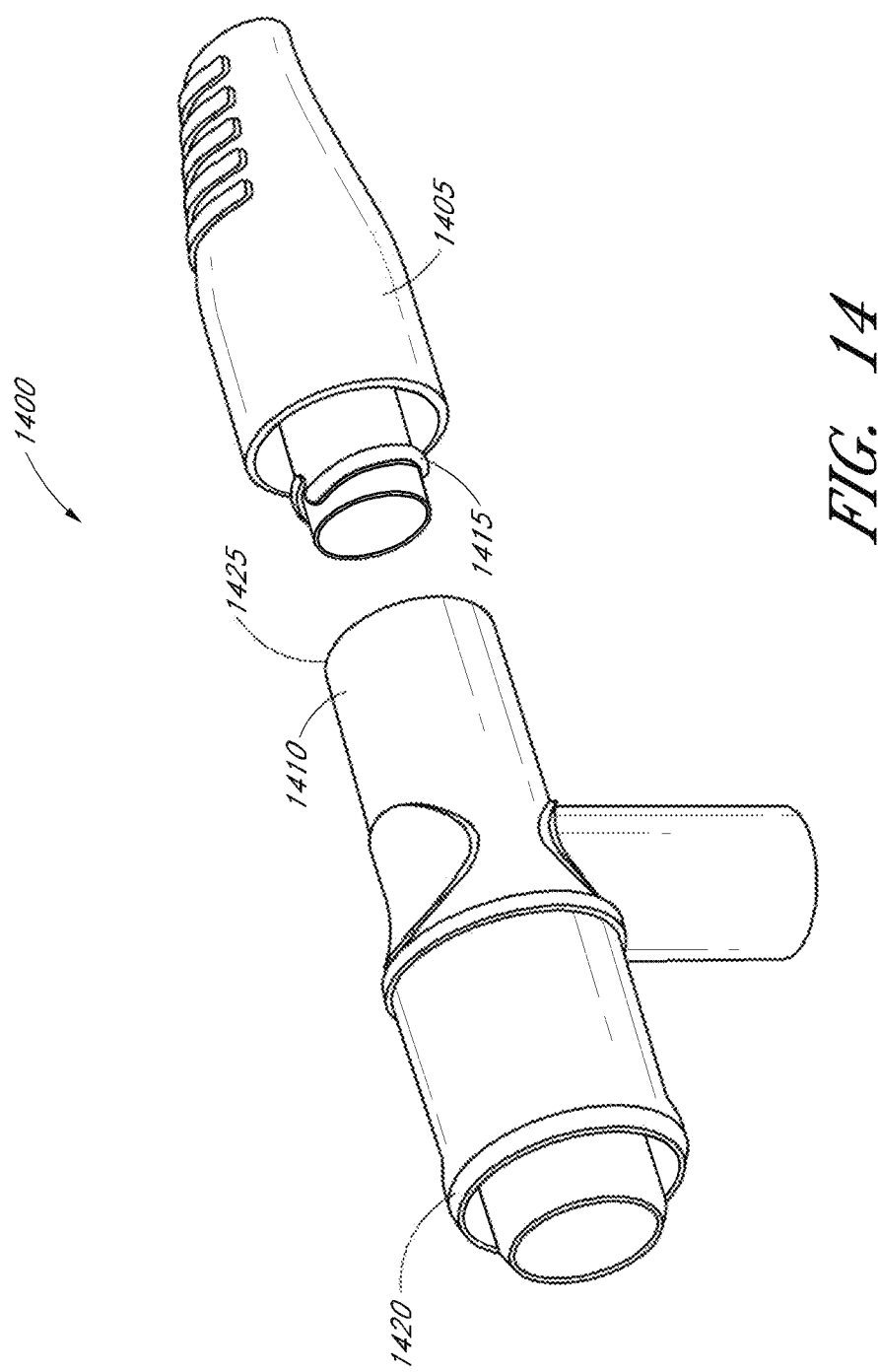

FIG. 14 illustrates another alternate connector embodiment 1400 of the connector of FIG. 1A. In FIG. 14, a terminal conduit connector 1405 connects to a source conduit connector 1410. A locking thread 1415 formed on a connecting end of the terminal conduit connector engages with the source conduit connector. Twisting the terminal conduit connector 1405 relative to the source conduit connector 1410 can cause the locking thread 1415 to disengage, allowing the connector 1400 to be separated.

In one embodiment, one side of the conduit connector 1410 can be configured to engage with another component using a unique or proprietary connection mechanism while the other side of the conduit connector 1410 uses a generic or standard connection mechanism. The generic connection can allow connection to a variety of components, made by different manufacturers. Meanwhile, the proprietary connection only allows connection to components of a single or a select set of manufacturers. Providing two different types of connectors can be beneficial in situations when one component requires greater accuracy than another and requiring use of a particular component allows components with known or predetermined characteristics to be used. Meanwhile, the generic connection can provide greater interoperability. In one example embodiment, the generic connection 1420 attaches using a friction fit while the proprietary connection 1425 connects with the locking thread 1415.

Figure 15:
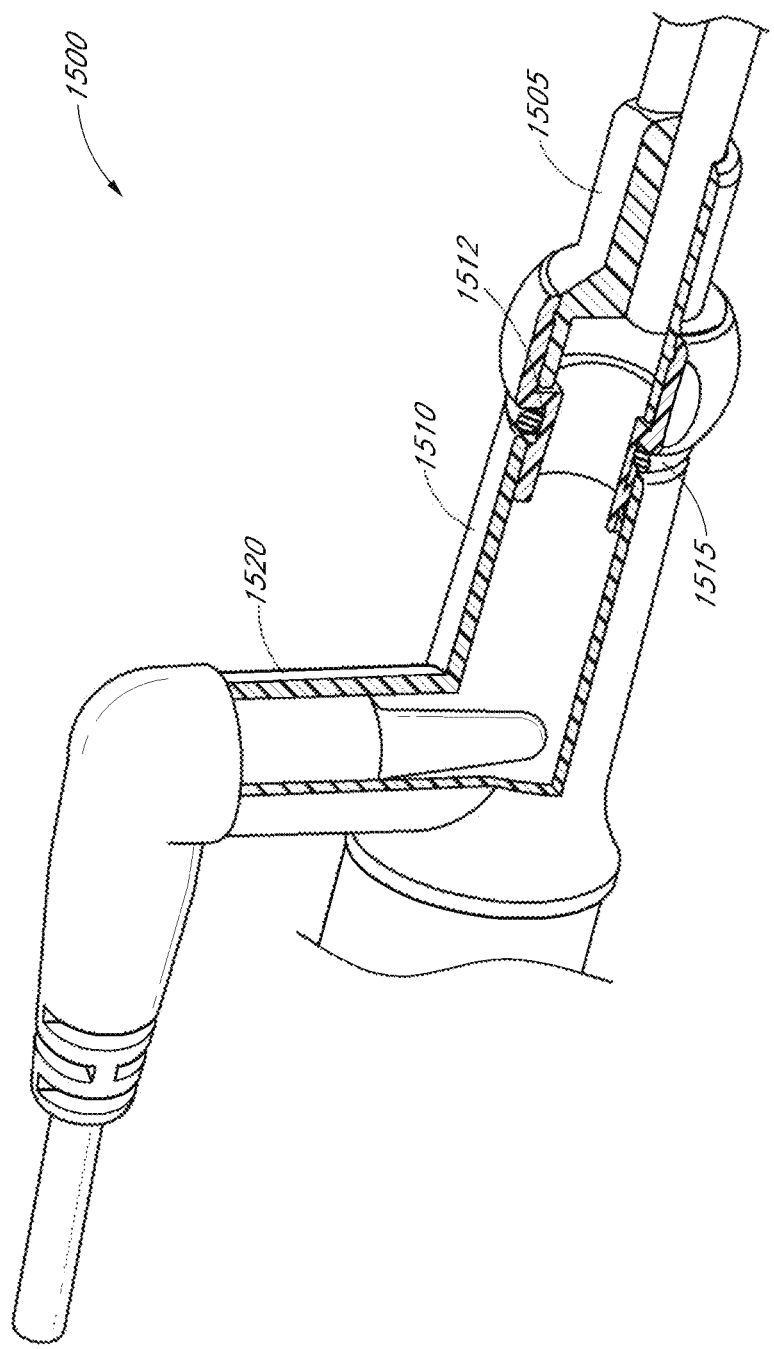

FIG. 15 illustrates another alternate connector embodiment 1500 of the connector of FIG. 1A. In FIG. 15, a terminal conduit connector 1505 connects a source conduit connector 1510. The edge of the source conduit connector 1510 can engage with a locking groove 1512 on the terminal conduit connecter 1505. An O-ring seal 1515 creates a seal between the terminal conduit connector and source conduit connector. In the illustrated embodiment, a sensor port 1520 is formed on the source conduit connector away from the source conduit connector's connection with the terminal conduit connector.

Figure 16:
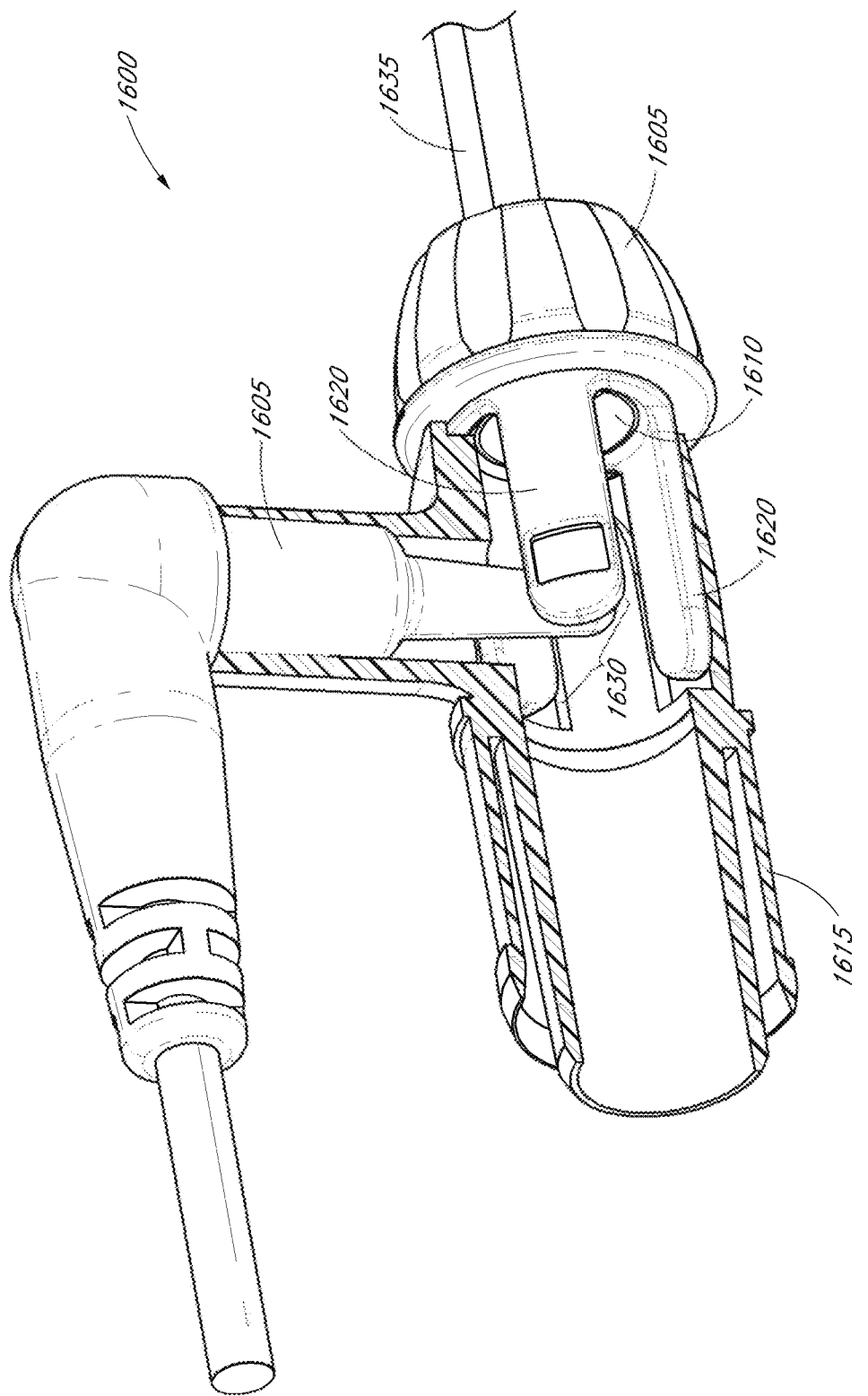

FIG. 16 illustrates another alternate connector embodiment 1600 of the connector of FIG. 1A. In FIG. 16, a terminal conduit connector 1605 connects with a connecting adapter 1610, which connects with a source conduit connector 1615. In the illustrated embodiment, the connecting adapter 1610 includes three fingers 1620 for engaging with the source conduit connector 1615. The fingers 1620 can be spaced apart to create an insertion aperture 1630 for a sensor probe 1605 to fit between two of the fingers 1620. The insertion aperture 1630 allows the sensor probe 1605 to be positioned closer to the nasal cannula 1635. For example, without the insertion aperture 1630, the sensor probe 1605 may have to be placed past the ends of the connecting adapter 1610, further away from the nasal cannula 1635.

Figure 17:
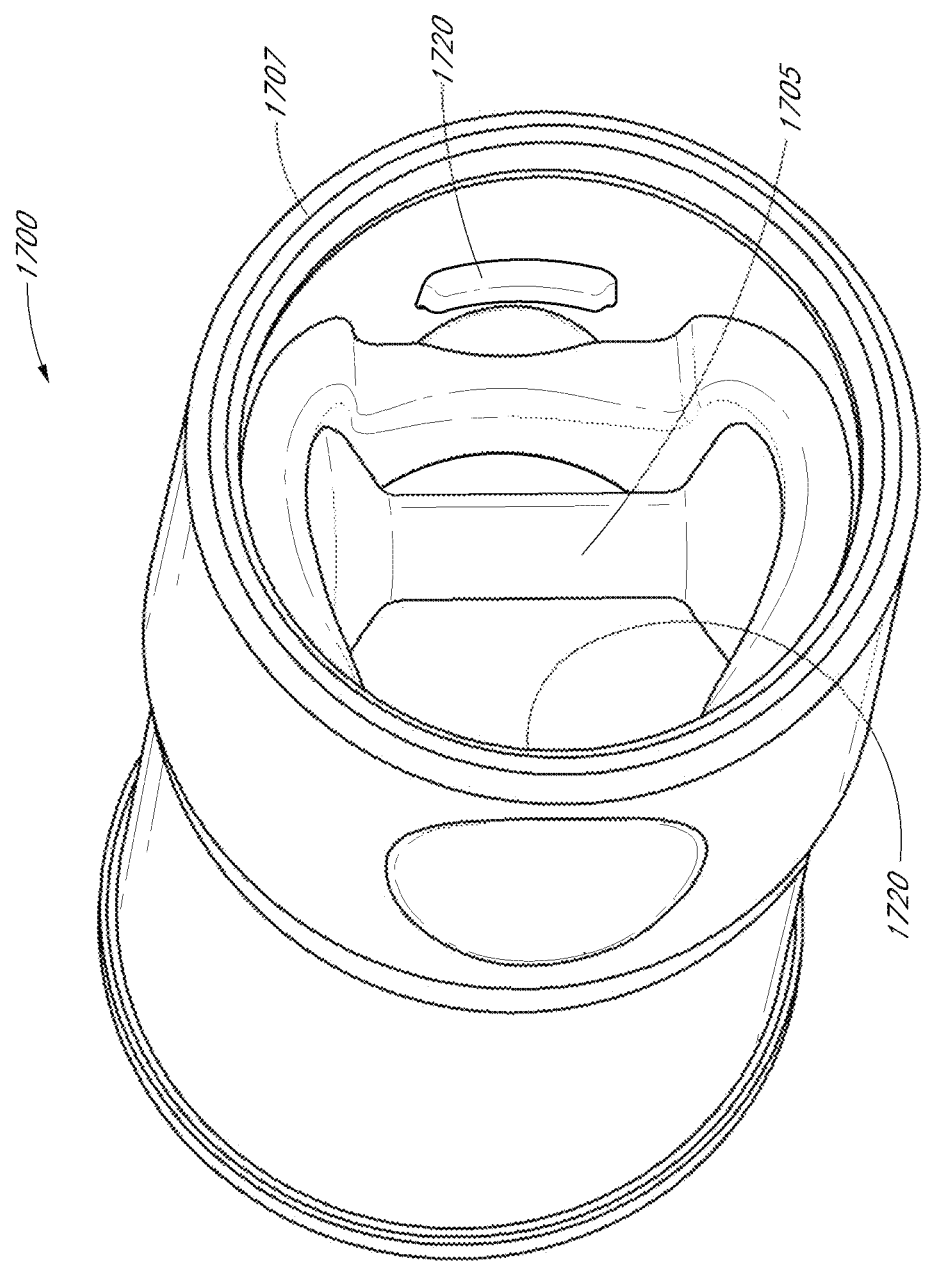
FIG. 17 illustrates an alternate conduit connector embodiment.

FIG. 17 illustrates an embodiment of a conduit connector 1700 having an integrated sensor probe 1705. The sensor probe 1705 is positioned to fit into an insertion aperture formed by two fingers of a connecting adapter (e.g., connecting adapter 140 of FIG. 1). By fitting into an insertion aperture, the sensor probe 1705 can be positioned closer to a nasal cannula. In the illustrated embodiment, the sensor probe 1705 is positioned at approximately the same distance from an aperture 1707 of the conduit connector 1700 as locking tabs 1720. The sensor probe 1705 fits between the fingers of the connecting adapter when the fingers engage with the locking tabs 1720. In one embodiment, the conduit connector 1700 does not have a sensor port.

Figure 18A:
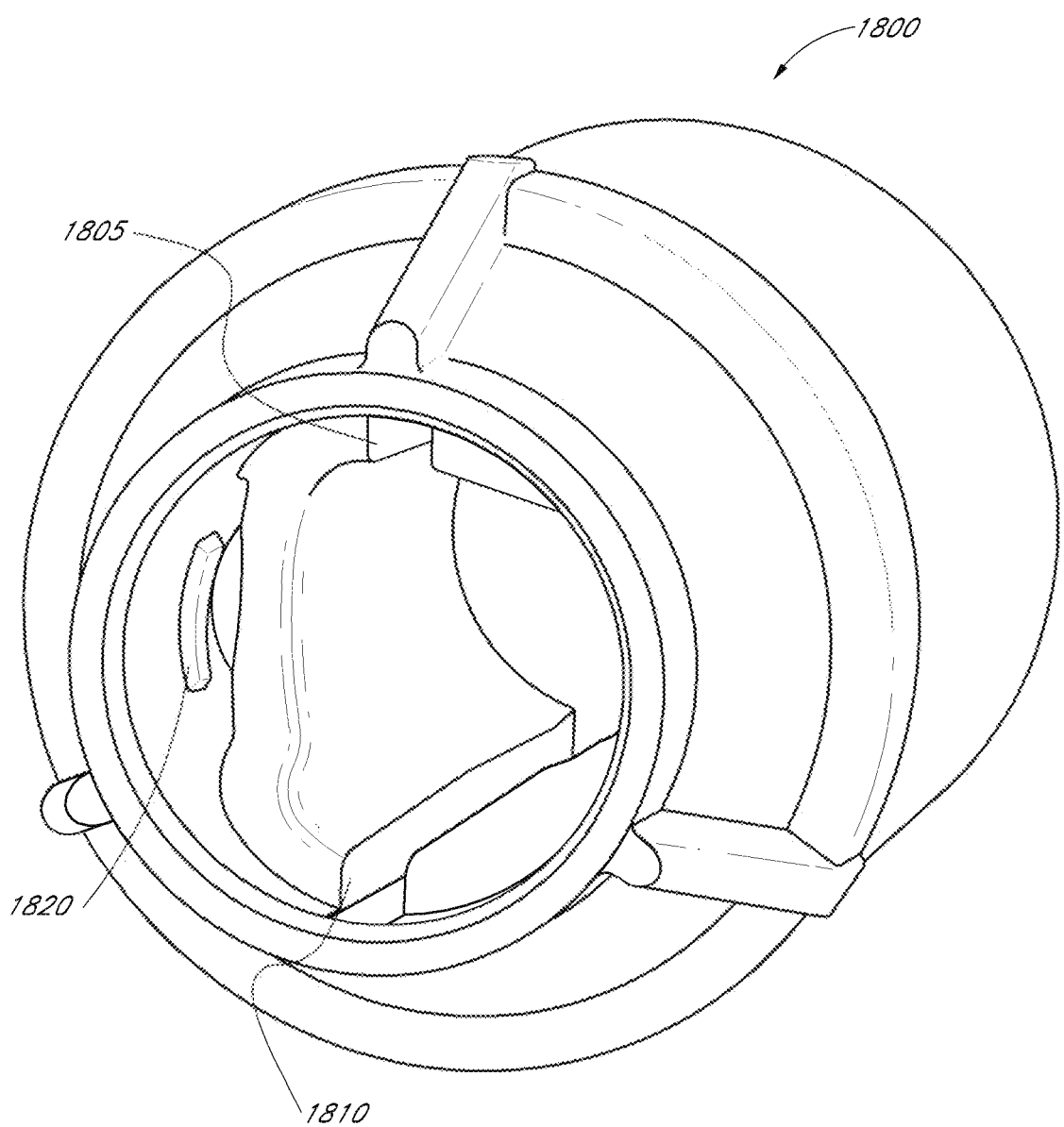
FIGS. 18A-18C illustrate different views of another alternate conduit connector embodiment.
Figure 18B:
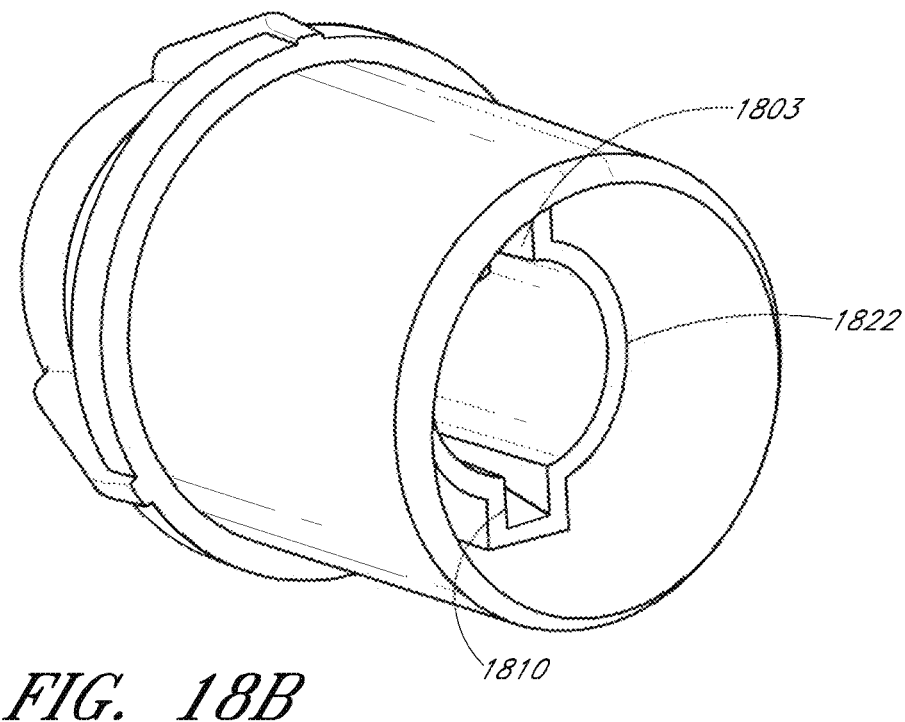
Figure 18C:
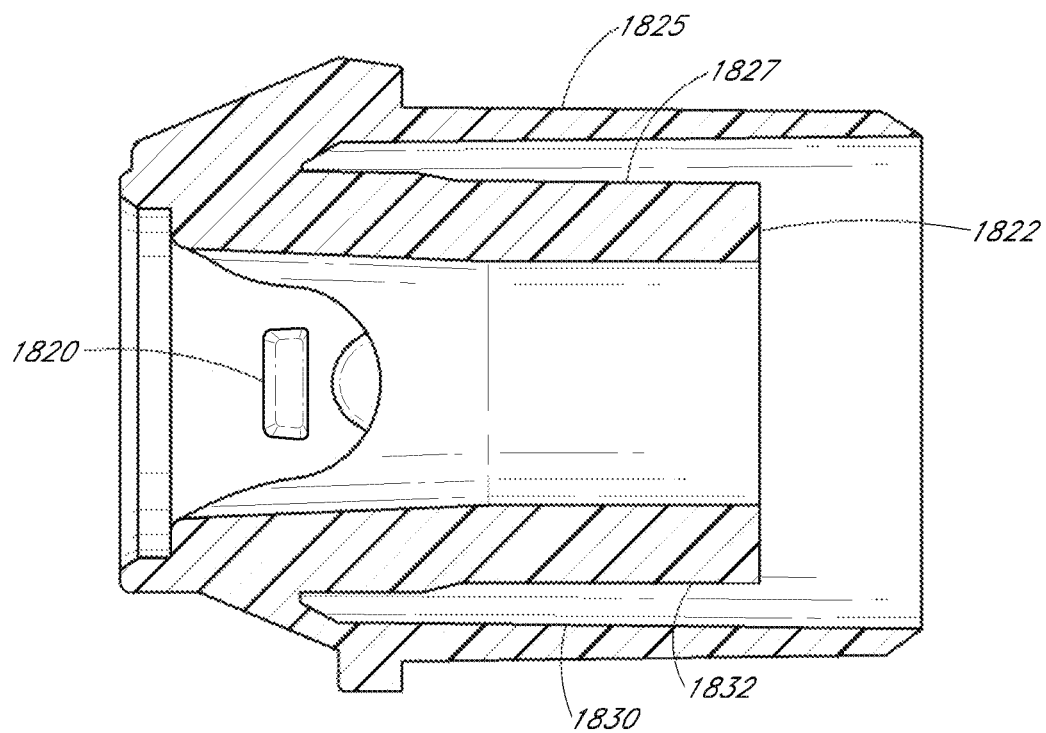

FIGS. 18A-18C illustrate different views of an embodiment of a conduit connector 1800 having a receptacle for a detachable sensor probe. In the illustrated embodiment of FIG. 18A, the receptacle includes channels 1805, 1810 for receiving the sensor probe. The channels 1805, 1810 can extend partially or wholly within an interior surface of the conduit connector 1800. The sensor probe can be plate-shaped, rectangular shaped, oval shaped, diamond shaped or any other shape configured to be received by the receptacle. In one embodiment, the sensor probe comprises alignment tabs configured to engage with the channels 1805, 1810. The alignment tabs can be configured to position the sensor probe into a predetermined position within the conduit connector 1800, such as a position where sensor measurements can be more effectively taken or a position between an insertion aperture formed by one or more locking fingers of a connecting adapter.

In one embodiment, the receptacle can include a catch, notch, tab, wall or other structure for locking or securing the sensor probe in place once the predetermined position is reached. In some embodiments, the receptacle can include other structures for receiving and/or securing the sensor probe in addition or alternatively to the channels 1805, 1810. For example, the receptacle can comprise ridges configured to engage with channels on the sensor probe. The conduit connector 1800 can also include one or more locking tabs 1820.

FIG. 18B illustrates a back perspective view and FIG. 18C illustrates a cross-sectional view of the embodiment of FIG. 18A. In the illustrated embodiment, an insertion groove for a second conduit, such as a hose or deliver tube, is formed by a space between the outer wall 1825, 1830 and an inner wall 1827, 1832 of the conduit connector 1800. In the illustrated embodiment, and end of the outer wall extends past an end 1822 of the inner wall. However, in other embodiments, the inner and outer wall may be the same length or the inner wall may extend past the outer wall.

Figure 19A:
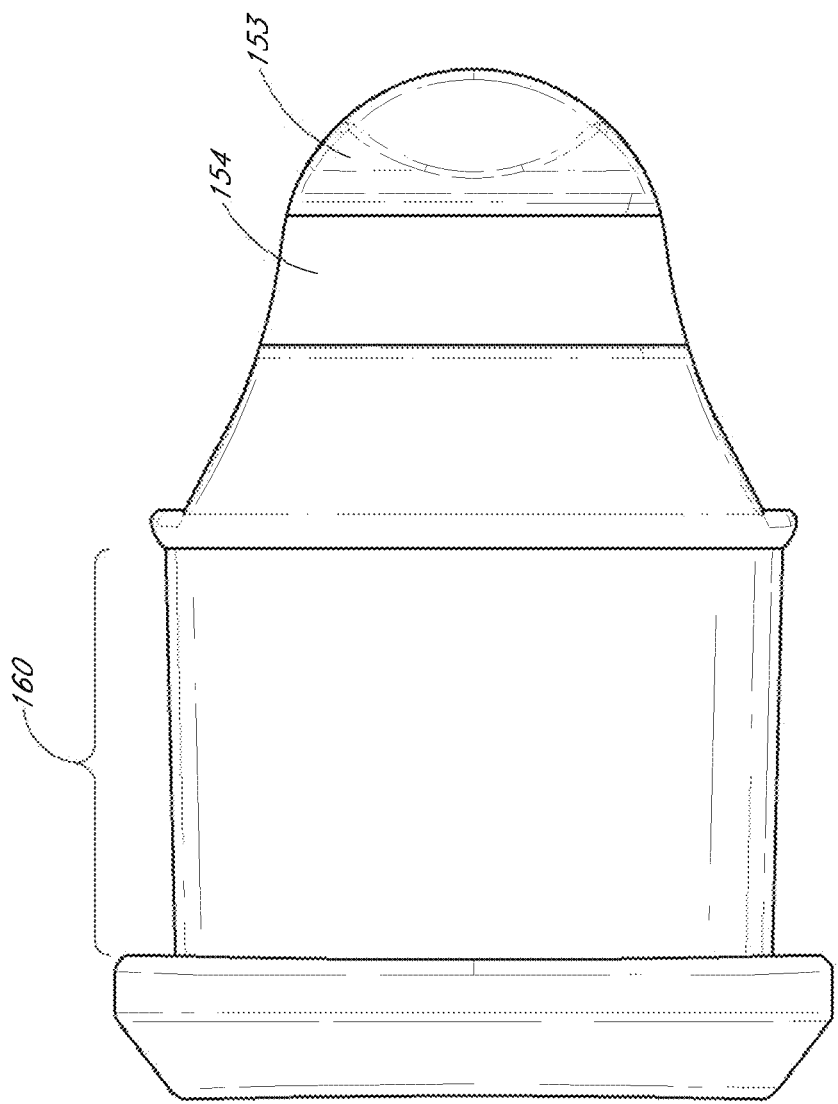
Figure 20A:
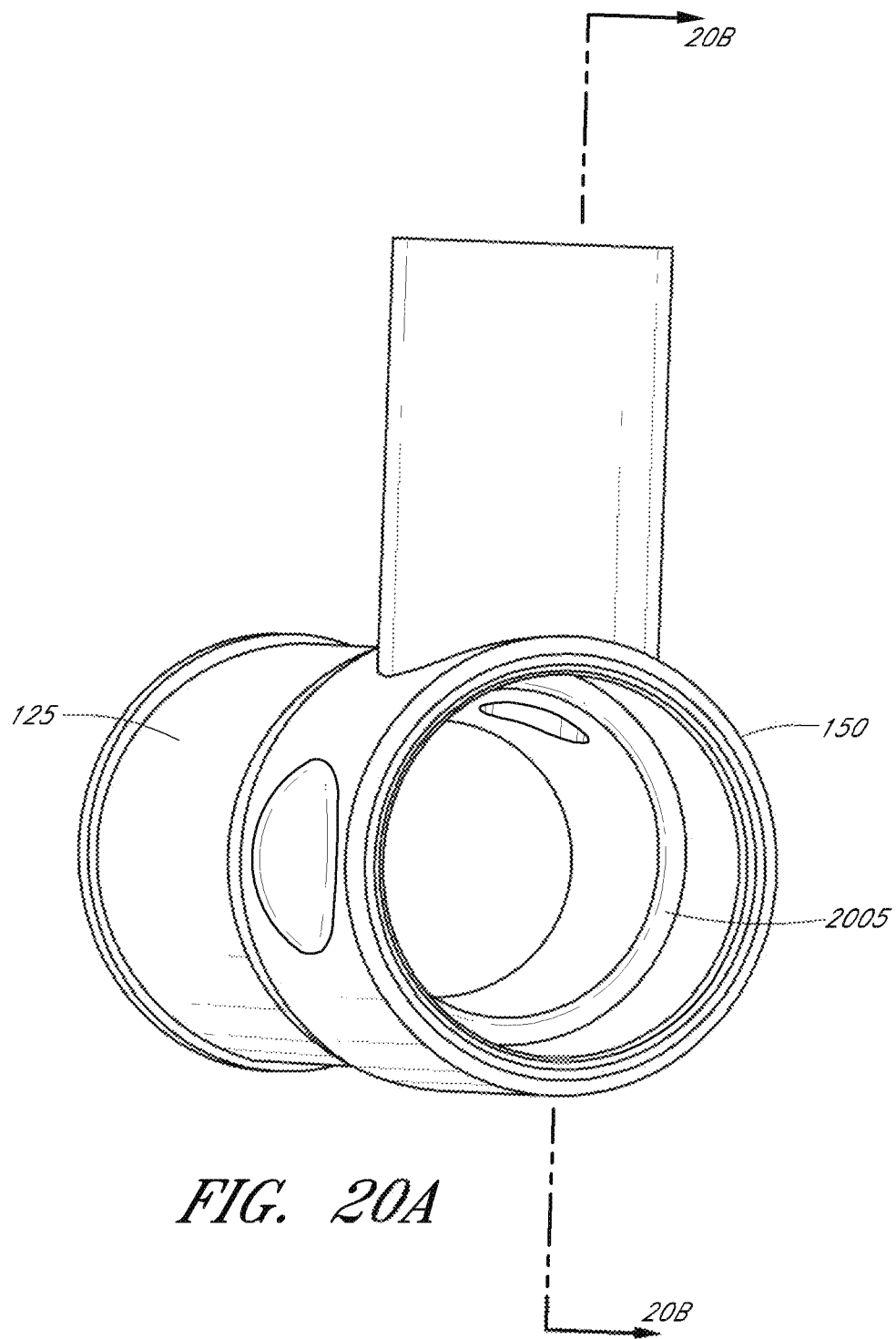

FIGS. 19A-19B illustrate an alternate connector adapter embodiment configured to connect with the source conduit connector embodiment of FIGS. 20A-20B.

FIG. 19A illustrates a side view of the connecting adapter facing one of two locking fingers 153 and its locking recess 154. A channel 160 formed on the body of the connecting adapter provides an engagement surface for a corresponding terminal conduit connector, as shown in various embodiments of the disclosure. In FIG. 19A, the locking recess 154 extends across the locking finger 153 to provide engagement with an annular locking ring on the source conduit connector embodiment of FIGS. 20A-20B.

FIG. 19B illustrates a perspective view of the connecting adapter of FIG. 19A showing the locking fingers 153 and its locking recess 154.

FIGS. 20A-20B illustrate an alternate source conduit connector 125 embodiment having an annular ring for attaching to the alternate connector adapter embodiment of FIGS. 19A-19B.

FIG. 20A illustrates a perspective view of the source conduit connector facing the terminal aperture 150 side. Formed within the interior surface of the source conduit connecter is an annular locking ring 2005 formed by a raised strip running circumferentially within the body of the source conduit connector. The locking recesses 154 of the connecting adapter of FIGS. 19A and 19B are configured to engage with the annular locking ring 2005 when the connecting adapter is inserted into the source conduit connector.

FIG. 20B illustrates a cross sectional view taken along the indicated cross section line in FIG. 20A. The cross-sectional view shows the annular locking ring 2005 formed on the interior surface of the source conduit connecter.

FIGS. 21A-D illustrate different views of an embodiment of a nasal cannula 2100 that connects to an airflow source via the various connector embodiments discussed in the disclosure. In some embodiments, the nasal cannula is for infants.

Figure 21A:
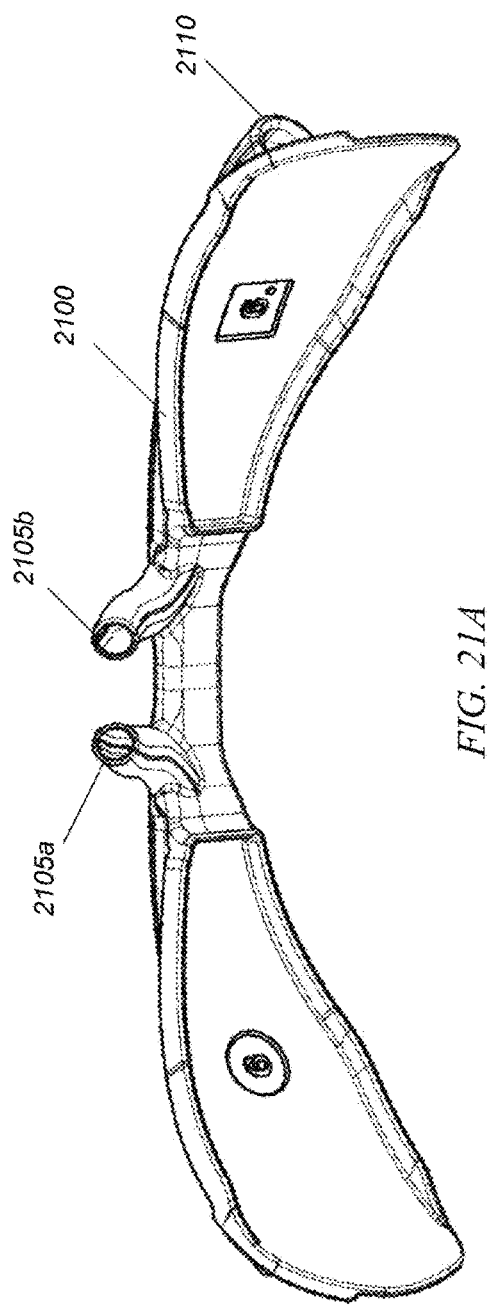
FIGS. 21A-D illustrate different views of an embodiment of a nasal cannula that connects to an airflow source via the various connector embodiments discussed in the disclosure.

FIG. 21A illustrates a top perspective view of the patient facing side of the nasal cannula 2100. The nasal cannula 2100 includes two prongs 2105*a*, 2105*b* that fit into the patient's nostrils. Airway tubes 2110 extend from the prongs and connect to an air source (e.g., via the connector 105 of FIG. 1A).

Figure 21B:
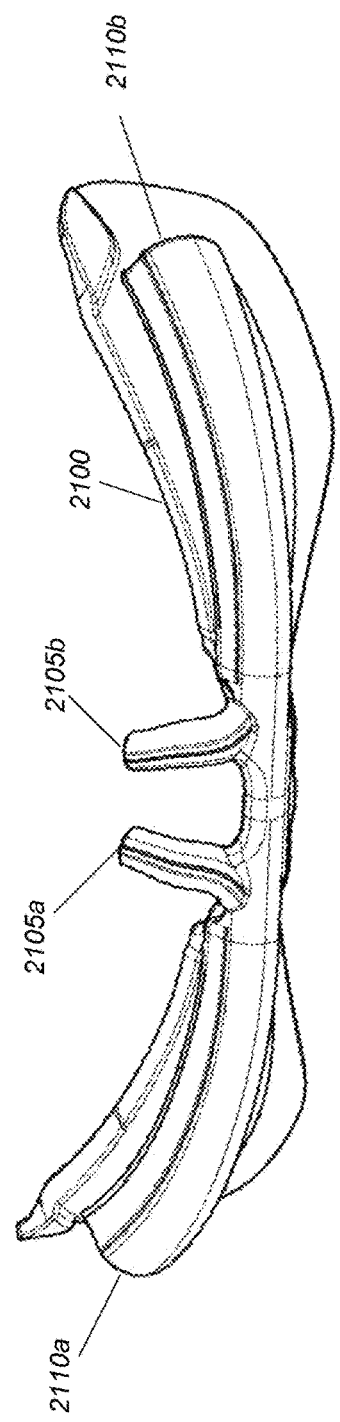

FIG. 21B illustrates a top perspective view of the external side of the nasal cannula 2100 facing away from the patient. FIG. 21B shows the two prongs 2105*a*, 2105*b* and two airway tubes 2110*a*, 2110*b* connected to the two prongs.

Figure 21C:
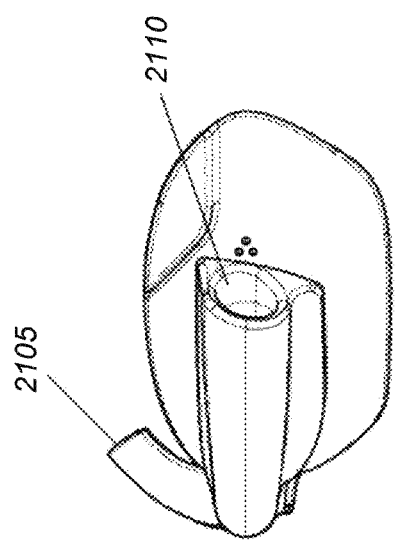

FIG. 21C illustrates a side view of the nasal cannula 2100 showing one of the prongs 2105 and one of the airway tubes 2110.

Figure 21D:
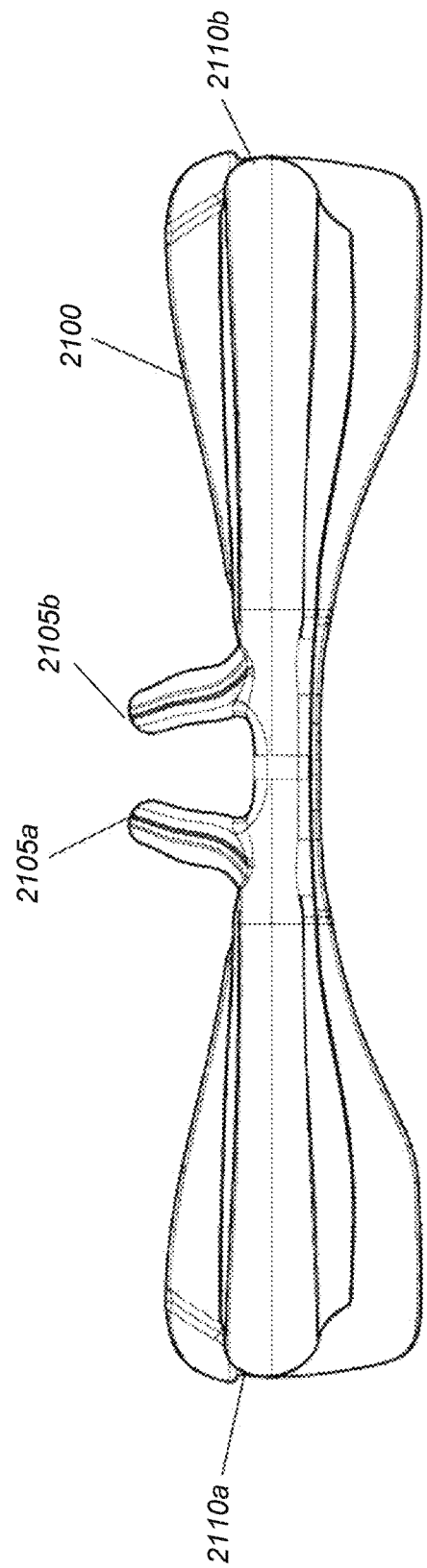

FIG. 21D illustrates a bottom view of the nasal cannula 2100 showing the two prongs 2105*a*, 2105*b* and the two airway tubes 2110*a*, 2110*b* connected to the two prongs.

In some embodiments, certain features can be associated with different components or left out. For example, the connection mechanism in the terminal conduit connector 120 can be implemented by the source conduit connector 125 and/or the connection mechanism of the source conduit connector 125 can be implemented by the terminal conduit connector 120. In another example, the sensor port 130 can be located on the terminal conduit connector 120 rather than the source conduit connector 125. Some features can be implemented by a different component (e.g., the terminal conduit connector 120, source conduit connector 125 or connecting adapter 140) rather than in the component described as implementing the feature in the above disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features and/or elements are in any way required for one or more embodiments.

Although the foregoing disclosure has been described in terms of certain preferred embodiments, other embodiments will be apparent to those of ordinary skill in the art from the disclosure herein. It is contemplated that various aspects and features of the disclosure described can be practiced separately, combined together, or substituted for one another, and that a variety of combination and subcombinations of the features and aspects can be made and still fall within the scope of the disclosure. Accordingly, the present disclosure is not intended to be limited by the recitation of the preferred embodiments, but is to be defined by reference to the appended claims.

What is claimed is:

1. A connector assembly, the connector assembly comprising:
   a connecting adapter; and
   a first connector for receiving the connecting adapter, wherein the first connector comprises:
      at least one ridge formed longitudinally on an inside surface of the connector, the at least one ridge configured to engage and lock with a locking channel formed on an outside surface of a connecting adapter body of the connecting adapter, the locking channel being defined by a cylindrical surface along a length of the connecting adapter body and raised edges on opposite ends of the cylindrical surface,
      a first closed-circle aperture configured to receive said connecting adapter, and
      at least one second closed-circle aperture, the second aperture configured to receive a conduit.

2. The connector of claim 1, wherein the first connector further comprises a locking groove formed around a circumference of the inside surface of the first connector, the locking groove configured to engage with a collar of the connecting adapter.

3. The connector of claim 1, wherein a collar of the connecting adapter is configured to prevent or inhibit disconnection of the at least one ridge due to longitudinal force, while allowing the at least one ridge to rotate along the locking channel.

4. The connector of claim 1, wherein the locking channel is configured to rotatably engage with said at least one ridge.

5. The connector of claim 1, wherein the connecting adapter provides for connection with a second connector.

6. The connector of claim 1, wherein the second aperture of the first connector is a terminal aperture configured to receive a conduit of a patient interface, or the first aperture of the first connector is a source aperture configured to receive a flow of gases.

7. The connector assembly of claim 1, wherein the connecting adapter comprises a connecting adapter body with one or more locking fingers configured to releasably attach to a second connector, the one or more locking fingers protruding longitudinally from the connecting adapter body.

8. The connector assembly of claim 1, wherein the connecting adapter further comprises one or more locking recesses formed on respective locking fingers, the one or more locking recesses configured to engage with locking tabs formed on a second connector.

9. The connector assembly of claim 8, wherein the respective locking fingers are configured to interact with one or more alignment tabs on the second connector such that the one or more locking recesses are aligned with one or more locking tabs on the second connector when the connecting adapter is connected to the second connector.

10. The connector assembly of claim 1, wherein the connecting adapter is rotatable relative to the first connector when the first connector is engaged with the connecting adapter.

11. A connector assembly, the connector assembly comprising:
a first connector configured to provide gases to a patient interface, the first connector comprising:
at least one ridge formed longitudinally on an inside surface of the first connector,
a first aperture configured to receive a connecting adapter, and
at least one second aperture configured to receive a conduit;
a connecting adapter, the connecting adapter comprising:
a connecting adapter body, and
one or more locking fingers, the one or more locking fingers configured to releasably attach to a second connector, the one or more locking fingers protruding longitudinally from the connecting adapter body,
one or more locking recesses formed on the respective locking fingers, the one or more locking recesses configured to engage with one or more locking tabs formed on the second connector, and
a locking channel formed on an outside surface of the connecting adapter body, said locking channel configured to rotatably engage and lock with the at least one ridge of the first connector; and
the second connector, the second connector comprising a first aperture configured to connect with an airflow source, and a second aperture configured to receive the connecting adapter, the second connector further comprising the one or more locking tabs configured to releasably attach with the one or more locking fingers of the connecting adapter.

12. The connector assembly of claim 11, wherein the first connector comprises a locking groove formed around a circumference of the inside surface of the first connector, the locking groove configured to engage with a collar of the connecting adapter.

13. The connector assembly of claim 11, wherein a collar of the connecting adapter is configured to prevent or inhibit disconnection of the at least one ridge due to longitudinal force, while allowing the at least one ridge to rotate along the locking channel.

14. The connector assembly of claim 11, wherein the second connector further comprises an alignment tab formed on an interior surface of the second connector, the alignment tab configured to automatically align the one or more locking fingers of the connecting adapter with the one or more locking tabs of the second connector upon insertion of the connecting adapter within the second connector.

15. The connector assembly of claim 14, wherein the alignment tab is configured to automatically align the one or more locking fingers of the connecting adapter with the one or more locking tabs of the second connector by causing the connecting adapter to rotate relative to the second connector upon insertion of the connecting adapter within the second connector.

16. The connector assembly of claim 11, wherein the connector assembly creates a seal between the first connector and the second connector.

17. The connector assembly of claim 11, wherein the second aperture of the first connector is a terminal aperture configured to receive a conduit of the patient interface, or wherein the first aperture of the first connector is a source aperture configured to receive a flow of gases.

18. The connector assembly of claim 11, wherein the connecting adapter is rotatable relative to the first connector when the first connector is engaged with the connecting adapter.

19. The connector assembly of claim 11, wherein the connector assembly is configured to connect the patient interface to the airflow source.

20. The connector assembly of claim 19, wherein the patient interface is a nasal cannula.

* * * * *